United States Patent [19]
Langley et al.

[11] Patent Number: 5,913,768
[45] Date of Patent: Jun. 22, 1999

[54] PARTICLE FILTER APPARATUS

[75] Inventors: Robert Langley, Westminster; Dennis Hlavinka, Golden; Linda A. Taylor, Littleton; John C. Walker, Boulder, all of Colo.

[73] Assignee: Cobe Laboratories, Inc., Lakewood, Colo.

[21] Appl. No.: 08/676,039

[22] Filed: Jul. 5, 1996

Related U.S. Application Data

[62] Division of application No. 08/423,583, Apr. 18, 1995, abandoned.

[51] Int. Cl.$^6$ .............................. B04B 1/00; B04B 11/02
[52] U.S. Cl. ...................... 494/7; 494/5; 494/6; 494/45
[58] Field of Search .................................. 210/360.1, 97, 210/143, 787, 789, 782; 422/72; 494/5, 6, 7, 37, 8, 9, 45

[56] References Cited

U.S. PATENT DOCUMENTS

| | | | |
|---|---|---|---|
| 2,616,619 | 11/1952 | MacLeod . | |
| 3,825,175 | 7/1974 | Sartory | 494/36 |
| 4,091,989 | 5/1978 | Schlutz . | |
| 4,187,979 | 2/1980 | Cullis et al. | 604/6 |
| 4,268,393 | 5/1981 | Persidsky et al. | 210/516 |
| 4,269,718 | 5/1981 | Persidsky | 210/787 |
| 4,316,576 | 2/1982 | Cullis et al. . | |
| 4,322,298 | 3/1982 | Persidsky | 210/787 |
| 4,350,283 | 9/1982 | Leonian | 422/72 |
| 4,416,654 | 11/1983 | Schoendorfer et al. | 494/10 |
| 4,425,112 | 1/1984 | Ito | 494/18 |
| 4,425,172 | 1/1984 | Schirmer | 156/187 |
| 4,464,167 | 8/1984 | Schoendorfer et al. | 604/6 |
| 4,675,117 | 6/1987 | Neumann et al. | 210/789 |
| 4,680,025 | 7/1987 | Kruger et al. | 604/6 |
| 4,701,267 | 10/1987 | Watanabe et al. | 210/806 |
| 4,708,710 | 11/1987 | Dunn, Jr. | 494/37 |
| 4,708,712 | 11/1987 | Mulzet | 494/45 |

(List continued on next page.)

FOREIGN PATENT DOCUMENTS

| | | |
|---|---|---|
| 0 406 485 | 1/1991 | European Pat. Off. . |
| 0 408 462 | 1/1991 | European Pat. Off. . |
| 0 419 346 | 3/1991 | European Pat. Off. . |
| 37 00 122 | 7/1988 | Germany . |
| 3734170 | 4/1989 | Germany . |
| 1091071 | 5/1984 | U.S.S.R. . |
| 1236366 | 6/1986 | U.S.S.R. . |
| 1255136 | 9/1986 | U.S.S.R. . |
| 1725117 | 4/1992 | U.S.S.R. . |
| WO 94/02157 | 2/1994 | WIPO . |
| WO 94/27698 | 12/1994 | WIPO . |
| WO 96/40402 | 12/1996 | WIPO . |
| WO 97/30748 | 8/1997 | WIPO . |

OTHER PUBLICATIONS

Aart Plas, Theo de Witte, Hans Wessels, and Clements Haanen, "A New Multichamber Counterflow Centrifugation Rotor with High-separation Capacity and Versatile Potentials," Experimental Hematology 16:355–359 (1988) International Society for Experimental Hematology.

Michael G. Kauffman, Stephen J. Noga, Thomas J. Kelly, and Albert D. Donnenberg "Isolation of Cell Cycle Fractions by Counterflow Centrifugal Elutriation," Analytical Biochemistry 191, 41–46 (1990).

(List continued on next page.)

*Primary Examiner*—John Kim
*Attorney, Agent, or Firm*—Finnegan, Henderson, Farabow, Garrette & Dunner, L.L.P.

[57] ABSTRACT

An apparatus and method are disclosed for filtering or separating particles. The apparatus has a motor coupled to a centrifuge rotor rotatable about an axis of rotation. A fluid chamber rotates with the rotor. A substance is supplied to the inlet of the chamber. At least one of the motor and the substance supply are controlled to maintain a saturated fluidized bed of first particles within the fluid chamber while causing second particles to be retained in the chamber.

24 Claims, 10 Drawing Sheets

U.S. PATENT DOCUMENTS

| | | |
|---|---|---|
| 4,798,579 | 1/1989 | Penhasi ................................. 494/18 |
| 4,808,151 | 2/1989 | Dunn, Jr. et al. ......................... 604/6 |
| 4,851,126 | 7/1989 | Schoendorfer ...................... 210/651 |
| 4,885,137 | 12/1989 | Lork .................................. 422/140 |
| 4,936,820 | 6/1990 | Dennehey et al. ....................... 494/1 |
| 4,936,998 | 6/1990 | Nishimura et al. ................. 210/638 |
| 4,939,081 | 7/1990 | Figdor et al. ........................... 435/2 |
| 4,939,087 | 7/1990 | Van Wie et al. ...................... 435/813 |
| 5,078,671 | 1/1992 | Dennehey et al. ..................... 494/27 |
| 5,089,146 | 2/1992 | Carmen et al. ..................... 210/782 |
| 5,100,564 | 3/1992 | Pall et al. ............................. 210/782 |
| 5,213,970 | 5/1993 | Lopez-Berestein et al. ......... 435/240.2 |
| 5,224,921 | 7/1993 | Dennehey et al. .................... 494/18 |
| 5,229,012 | 7/1993 | Pall et al. ............................. 210/767 |
| 5,282,982 | 2/1994 | Wells ................................... 210/800 |
| 5,298,171 | 3/1994 | Biesel .................................. 210/739 |
| 5,316,666 | 5/1994 | Brown et al. ........................... 210/85 |
| 5,316,667 | 5/1994 | Brown et al. ........................... 210/85 |
| 5,360,542 | 11/1994 | Williamson, IV et al. ............ 210/232 |
| 5,362,291 | 11/1994 | Williamson, IV ..................... 494/18 |
| 5,370,802 | 12/1994 | Brown .................................. 210/782 |
| 5,397,479 | 3/1995 | Kass et al. ............................ 210/728 |
| 5,409,813 | 4/1995 | Schwartz ............................. 210/660 |
| 5,437,624 | 8/1995 | Langley ................................... 604/4 |
| 5,501,795 | 3/1996 | Pall et al. ............................. 210/508 |
| 5,529,691 | 6/1996 | Brown ................................... 210/94 |
| 5,547,591 | 8/1996 | Hagihara et al. .................... 210/782 |
| 5,549,834 | 8/1996 | Brown .................................. 210/806 |
| 5,580,465 | 12/1996 | Pall et al. ............................. 210/767 |
| 5,587,070 | 12/1996 | Pall et al. ............................. 210/202 |
| 5,607,830 | 3/1997 | Biesel et al. ............................. 435/2 |
| 5,622,819 | 4/1997 | Herman .................................. 435/4 |
| 5,641,414 | 6/1997 | Brown .................................. 210/782 |
| 5,643,786 | 7/1997 | Cohen et al. ......................... 435/325 |
| 5,674,173 | 10/1997 | Hlavinka et al. ....................... 494/17 |
| 5,690,602 | 11/1997 | Brown et al. .......................... 494/45 |
| 5,702,357 | 12/1997 | Bainbridge et al. ...................... 604/4 |
| 5,704,889 | 1/1998 | Hlvanika et al. ........................ 494/37 |
| 5,722,926 | 3/1998 | Hlavinka et al. ........................ 494/37 |

OTHER PUBLICATIONS

A. Faradji, A. Bohbot, M. Schmitt–Goguel, J.C. Siffert, S. Dumont, M.L. Wiesel, Y. Piemont, A. Eischen, J.P. Bergerat J. Bartholeyns, P. Poindron, J.P. Witz, F. Oberling, "Large Scale Isolation of Human Blood Monocytes by Continuous Flow Centrifugation Leukapheresis and Counterflow Centrifugation Elutriation for Adoptive Cellular Immunotherapy in Cancer Patients," Journal of Immunological Methods 174 (1994) 297–309.

Ino K. Gao, Stephen J. Noga, John E. Wagner, Carol A. Cremo, Janice Davis, and Albert D. Donnenberg, "Implementation of a Semiclosed Large Scale Counterflow Centrifugal Elutriation System," Journal of Clinical Apheresis 3:154–160 (1987).

Owen M. Griffith, "Separation of T and B Cells from Human Peripheral Blood by Centrifugal Elutriation," Analytical Biochemistry 87, 97–107 (1978).

Carl G. Figdor, Willy S. Bont, Ivo Touw, Johan de Roos, Eddy E. Roosnek, and Jan E. de Vries, "Isolation of Functionally Different Human Monocytes by Counterflow Centrifugation Elutriation," Blood, vol. 60, No. 1, 46–53 (1982).

Maxim D. Persidsky et al., Separation of Platelet–Rich Plasma by Modified Centrifugal Elutriation; Journal of Clinical Apheresis 1:18–24 (1982).

John F. Jemionek et al., Special Techniques for the Separation of of Hemopoietic Cells, Current Methodology in Experimental Hematology, 1984, pp. 12–16, Karger, New York.

J. Freedman et al., White cell depletion of red cell and pooled random–donor platelet concentrates by filtration and residual lymphocyte subset analysis, Transfusion, 1991, vol. 31, No. 5, pp. 433–440.

Nancy M. Heddle et al., The Role of the Plasma From Platelet Concentrates in Transfusion Reactions, The New England Journal of Medicine, vol. 331, No. 10, Sep. 8, 1994, pp. 625–628, 670 and 671.

A. Bruil et al., Asymmetric membrane filters for the removal of leukocytes from blood, Journal of Biomed. Materials Research, vol. 25, 1459–1480, 1991.

Sunny Dzik, Leukodepletion Blood Filters: Filter Design and Mechanisms of Leukocyte Removal, Transfusion Medicine Reviews, Vol VII, No. 2, Apr. 1993, pp. 65–77.

Bernard J. Van Wie et al., The Effect of Hematocrit and Recycle on Cell Separations, Plasma Ther. Transfus. Technol. 1986; 7:373–388.

P.D. Drumheller et al., The Effects of RPM and Recycle on Separation Efficiency in Clinical Blood Cell Centrifuge, Journal of Biomechanical Engineering, Nov. 1987, vol. 109, pp. 324–329.

R. J. Oxford et al., Monitoring and Automated Optimization of a Cell Centrifuge, IEEE/Eighth Annual Conference of the Engineering in Medicine and Biology Society, pp. 925–927 (undated).

R. J. Oxford et al., Interface dynamics in a centrifugal cell separator, Transfusion, Nov.–Dec., 1988, vol. 28, No. 6, pp. 588–592.

A. Tulp et al., A Separation Chamber to Sort Cells and Cell Organelles by Weak Physical Forces, V.A. Sector–Shaped Chamber and Its Application to the Separation of Peripheral Blood Cells, Journal of Immunolgical Methods 69 (1984), pp. 281–295.

Robert J. Grabske, Separating Cell Populations by Elutriation, pp. 1–8, Beckman.

Carl G. Figdor et al., Theory and Practice of Centrifugal Elutriation (CE) Factors Influencing the Separation of Human Blood Cells, Cell Biophysics 5, 105–118 (1983).

P.E. Lindahl, On Counter Streaming Centrifugation in the Separation of Cells and Cell Fragments, pp. 411–415, Biochemica et Biophysica, vol. 21 (1956).

C. Almici et al., Counterflow centrifugal elutriation: present and future, Bone Marrow Transplantation 1993, 12:105–108.

Richard J. Sanderson, Separation of Different Kinds of Nucleated Cells from Blood by Centrifugal Elutriation, Cell Separation Methods and Selected Applications, vol. 1, pp. 153–168 (undated).

P.C. Keng et al., Characterization of the Separation Properties of the Beckman Elutriator System, Cell Biophysics 3 (1981), pp. 41–56.

Biofil, Systems for Filtration of Haemocomponents (undated).

Claes F. Högman, Leucocyte Depletion of Blood Components, 1994 pp. 1, 156–173, Vu University Press, Amsterdam (1994).

A. S. Buchanan et al., Principle of a Counter–streaming Centrifuge for the Separation of Particles of Different Sizes, Nature, Apr. 24, 1948, pp. 648–649.

"Cost–Effectiveness of Leukocyte Depletion of Blood Components", Presented at the 1993 AABB Meeting Miami Beach, FL.

I. Sniecinski, Prevention of immunologic and infectious complications of transfusion by leukocyte depletion, Prevention of complications of transfusion Chapter 18; pp. 202–211 (undated).

Benefits of Leukocyte Filtration for Red Cell and Platelet Blood Products, Transfusion Associated CMV, pp. 1–18, Pall Biomedical Products Company, New York (1994).

G. Stack et al., Cytokine generation in stored platelet concentrates, Transfusion, 1994; 34:20–25.

N. M. Heddle et al., A prospective study to identify the risk factors associated with acute reactions to platelet and red cell transfusions; Transfusion, 1993; 33:794–797.

H. Brandwein et al., Asahi Sepacell PL10A Leukocyte Removal Filter: Efficiency with Random Donor Platelet Pools, PALL Technical Report (undated).

J. Whitbread et al., Performance Evaluation of the Sepacell PL10A filter and Pall PXL 8 filter: Measurement of Leukocyte Residuals and Consistency, PALL Technical Report, Pall Corporation, New York (undated).

R. Brown et al., Evaluation of a new separation method utilizing plasma recirculation and autoelutration, Transfusion, 1994; vol. 34, Supp. S237.

Richard J. Sanderson et al., Design Principles for a Counterflow Centrifugation Cell Separation Chamber; Analytical Biochemistry 71, 615–622(1976).

Designed to Provide the Reliability and Performance to Harvest a High Yield Component Product, The Haemonetics V50 Apheresis System (undated).

Haemonetics Mobile Collection System Owner's Operating and Maintenance Manual, 1991 pp. 3–2 through 3–7 and pp. 1–6, Haemonetics Corporation, MA.

E.A. Burgstaler et al., White Blood Cell Contamination of Apheresis Platelets Collected on the COBE Spectra, COBE Blood Component Technology, Co. (1990).

T.H. Price et al., Platelet Collection Using the COBE Spectra, COBE Blood Component Technology, COBE Laboratories, Inc. (1989).

Nancy Besso et al., Asahi Sepacell PL–10A Leukocyte Removal Filter: Effect of Post–Filtration Flush With Saline, PALL Technical Report, Pall Corporation (1991).

Harvey J. Brandwein et al., Asahi Sepacell PL–10A Leukocyte Removal Filter Description and Review of Claims, PALL Technical Report, Pall Corporation (1991).

"Lower is Better!", (flyer) PALL Biomedical Products Company, Pall Corporation (1994).

Judy H. Angelbeck, Adverse Reactions to Platelet Transfusion, Risks and Probable Causes pp. 1–14, Pall Corporation (1994).

Centrifugual Elutriation, Beckman pp. 1–7, Beckman pp. 1–7, Beckman Instruments Inc. (undated).

AS 104 Cell Separator, Fresenius AG, Germany (undated).

CS–3000 Blood Cell Separator, Powerful Technology, Fenwal Labratories (undated).

Baxter CS–3000 Puls Blood Cell Separator Operator's Manual (7–19–3–136).

The Mobile Collection System gives you easier access to more donors than ever before, Haemonetics Corporation (1992).

LRF6/LRF10, High Efficiency Leukocyte Removal Filter Systems For Platelets PALL Biomedical Products Corporation (undated).

J. Whitbread et al., Reducton of C3A Fragment Levels Following Leukodepletion Using a PALL PXL8 Filter, Pall Corporation (undated).

T. A. Takahashi et al., Bradykinin Formation in a Platelet Concentrate Filtered with a Leukocyte–removal Filter Made of Nonwoven Plyester Fibers with a Negatively Charged Surface, Red Cross Blood Center, Sapporo, Japan (undated).

Baxter CS–3000 Plus Blood Cell Separator pp. 1–18.

J. F. Jemionek, Variations in CCE Protocol for Cell Isolation, Elutriation, pp. 17–41 (undated).

Bernard John Van Wie, Conceptualization and Evaluation of Techniques for Centrifugal Separation of Blood Cells: Optimum Process Conditions, Recycle and Stagewise Processing, Dissertation, 1982, pp. 27–58, The University of Oklahoma.

Brief Operating Instructions, Fresenius MT AS 104 blood cell separator, 4/6.90(OP) (undated).

Multi Chamber Counterflow Centrifugation System, Dijkstra Vereenigde B.V., 6 pgs, Amsterdam, Netherlands (undated).

Baxter CS–3000 Plus Blood Cell Separator, Technology With a Mind You Can Own, 1990, pp. 1–18.

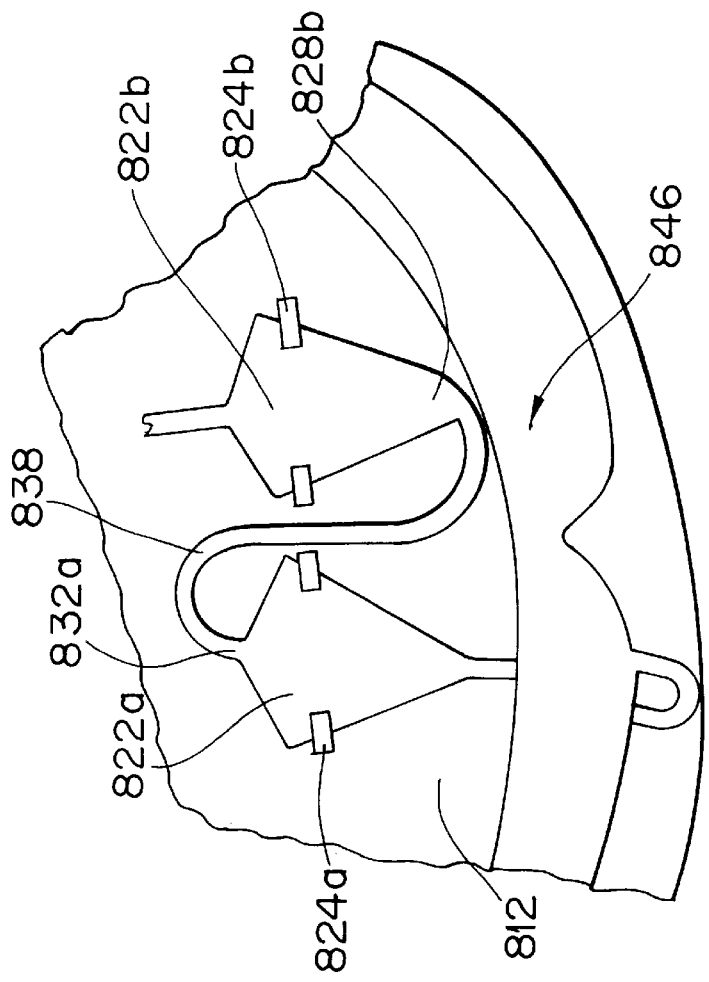
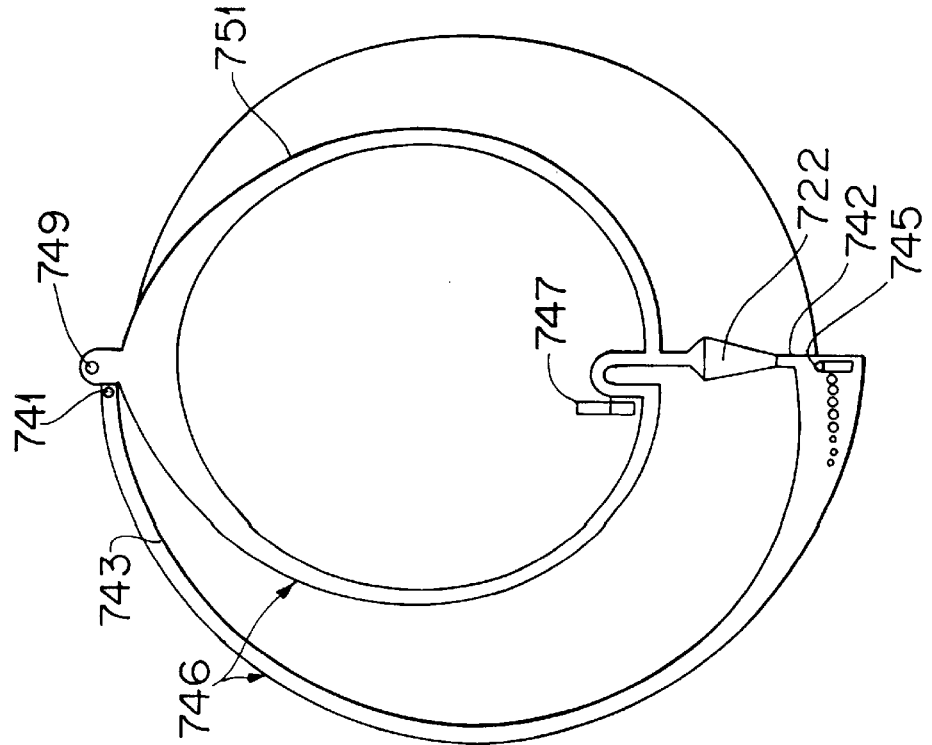
FIG. 14
FIG. 13

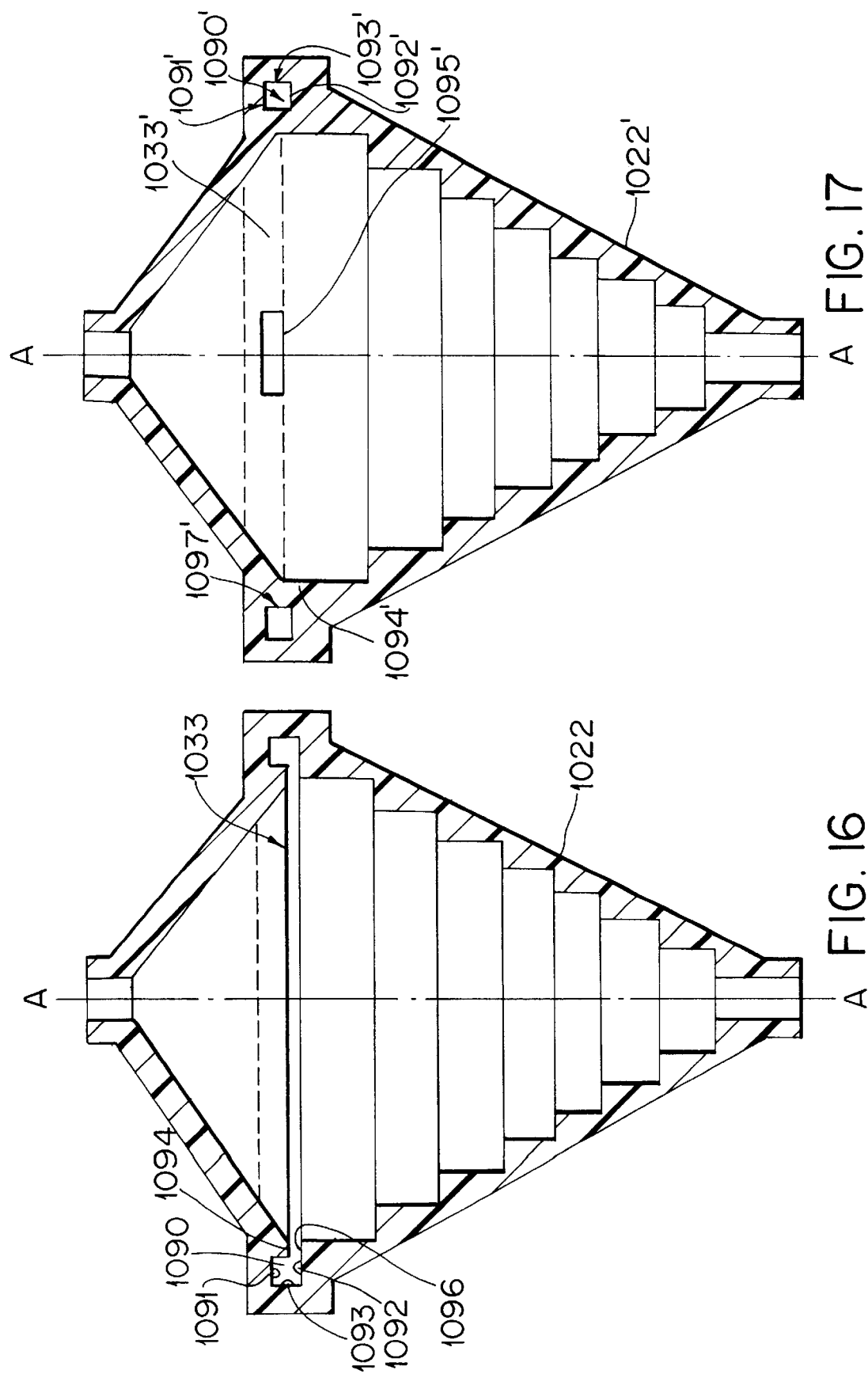

PARTICLE FILTER APPARATUS

This is a divisional application of application Ser. No. 08/423,583, filed Apr. 18, 1995, now abandoned.

BACKGROUND OF THE INVENTION

1. Field of the Invention

The present invention relates to an apparatus and method for filtering or separating particles from a liquid. The invention has particular advantages in connection with separating blood components.

2. Description of the Related Art

In many different fields, liquids carrying particle substances must be filtered or processed to obtain either a purified liquid or purified particle end product. In its broadest sense, a filter is any device capable of removing or separating particles from a substance. Thus, the term "filter" as used herein is not limited to a porous media material but includes many different types of processes where particles are either separated from one another or from liquid.

In the medical field, it is often necessary to filter blood. Whole blood consists of various liquid constituents and particle constituents. Sometimes, the particle constituents are referred to as "formed elements". The liquid portion of blood is largely made up of plasma, and the particle constituents include red blood cells (erythrocytes), white blood cells (including leukocytes), and platelets (thrombocytes). While these constituents have similar densities, their average density relationship, in order of decreasing density, is as follows: red blood cells, white blood cells, platelets, and plasma. In addition, these constituents are related according to size, in order of decreasing size, as follows: white blood cells, red blood cells, and platelets. Most current purification devices rely on these density and size differences or surface chemistry characteristics to separate and/or filter the blood components.

Numerous therapeutic treatments require groups of particles to be removed from whole blood before either liquid or particle components can be infused into a patient. For example, cancer patients often require platelet transfusions after undergoing ablative, chemical, or radiation therapy. In this procedure, donated whole blood is processed to remove platelets and these platelets are then infused into the patient. However, if a patient receives an excessive number of foreign white blood cells as contamination in a platelet transfusion, the patient's body may reject the platelet transfusion, leading to a host of serious health risks.

Typically, donated platelets are separated or harvested from other blood components using a centrifuge. The centrifuge rotates a blood reservoir to separate components within the reservoir using centrifugal force. In use, blood enters the reservoir while it is rotating at a very rapid speed and centrifugal force stratifies the blood components, so that particular components may be separately removed. Centrifuges are effective at separating platelets from whole blood, however they typically are unable to separate all of the white blood cells from the platelets. Prior art blood separation and centrifugation devices are typically unable to consistently (99% of the time) produce platelet product that meets the "leukopoor" standard of less than $5 \times 10^6$ white blood cells for at least $3 \times 10^{11}$ platelets collected.

Because typical centrifuge platelet collection processes are unable to consistently and satisfactorily separate white blood cells from platelets, other processes have been added to improve results. In one procedure, after centrifuging, platelets are passed through a porous woven or non-woven media filter, which may have a modified surface, to remove white blood cells. However, use of the porous filter introduces its own set of problems. Conventional porous filters may be inefficient because they may permanently remove or trap approximately 5–20% of the platelets. These conventional filters also reduce "platelet viability," meaning that once passed through a filter a percentage of the platelets cease to function properly and may be partially or fully activated. Porous filters are also expensive and often require additional time consuming manual labor to perform a filtration process.

Although porous filters are effective in removing a substantial number of white blood cells, they have drawbacks. For example, after centrifuging and before porous filtering, a period of time must pass to give activated platelets time to transform to a deactivated state. Otherwise, the activated platelets are likely to clog the filter. Therefore, the use of porous filters is not feasible in on-line processes.

Another separation process is one known as centrifugal elutriation which separates cells suspended in a liquid medium without a membrane filter. In one common form of this process, a cell batch is introduced into a flow of liquid elutriation buffer. This liquid having a cell suspension is then introduced into a funnel-shaped chamber located in a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

Thus, centrifugal elutriation separates particles having different sedimentation velocities. Stoke's law describes sedimentation velocity (SV) of a spherical particle as follows:

$$SV = \frac{2}{9} \frac{r^2(\sigma_p - \sigma_m)g}{\eta}$$

where, r is the radius of the particle, $\rho_p$ is the density of the particle, $\rho_m$ is the density of the liquid medium, $\eta$ is the viscosity of the medium, and g is the gravitational or centrifugal acceleration. Because the radius of a particle is raised to the second power in the Stoke's equation, while the density of the particle is not, the size of a cell, rather than its density, greatly influences its sedimentation rate. This explains why larger particles generally remain in a chamber during centrifugal elutriation, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

Further, a Coriolis jetting effect takes place when particles flow into an elutriation chamber from a high centrifugal field toward a lower centrifugal field. The fluid and particles turbulently collide with an inner wall of the chamber facing the rotational direction of the centrifuge. This phenomenon mixes particles within the chamber and reduces the effectiveness of the separation process. Further, Coriolis jetting shunts flow along the inner wall from the inlet directly to the outlet. Thus, particles pass around the elutriative field to contaminate the end product.

Particle mixing by particle density inversion is an additional problem encountered in some prior elutriation processes. Fluid flowing within the elutriation chamber has a decreasing velocity as it flows in the centripetal direction from an entrance port toward an increased cross sectional portion of the chamber. Because particles tend to concentrate within a flowing liquid in areas of lower flow velocity, rather than in areas of high flow velocity, the particles concentrate near the increased cross-sectional area of the chamber. Correspondingly, since flow velocity is greatest adjacent the entrance port, the particle concentration is reduced in this area. Density inversion of particles takes place when the centrifugal force urges the particles from the high particle concentration at the portion of increased cross-section toward the entrance port. This particle turnover reduces the effectiveness of particle separation by elutriation.

In view of the foregoing, for these and other reasons, there is a need to improve particle separation.

SUMMARY OF THE INVENTION

The present invention is directed to an apparatus and method that substantially obviate one or more of the limitations and disadvantages of the related art. To achieve these and other advantages and in accordance with the purpose of the invention, as embodied and broadly described herein, the invention comprises an apparatus for filtering first particles from a liquid. The apparatus includes a motor, and a centrifuge rotor coupled to the motor for rotation about an axis of rotation. A holder is provided for holding a fluid chamber on the rotor with an outlet of the fluid chamber positioned closer to the axis of rotation than an inlet of the fluid chamber. Means are provided for supplying a substance to the inlet of the fluid chamber, and means are also provided for controlling at least one of the motor and the supplying means to maintain a saturated fluidized bed of second particles within the fluid chamber and to cause first particles to be retained within the fluid chamber.

In another aspect, the invention includes a method of separating first particles from second particles. The method comprises the steps of rotating a centrifuge rotor about an axis of rotation, the rotor having a fluid chamber. With the method of the invention, rotation of the rotor is controlled and second particles are passed into an inlet of the fluid chamber. A saturated fluidized bed is formed within the chamber with the second particles. Liquid having at least first particles is flowed into the chamber inlet while maintaining the bed in the fluid chamber so that the bed substantially prevents flow of first particles from the inlet to the outlet while substantially permitting flow of liquid to the outlet.

When the method of the invention is used in connection with blood filtering, the liquid may include plasma and the first particles may be white blood cells, while the second particles may be platelets or red cells. Thus, the bed may filter and obstruct the passage of white blood cells.

Further, the invention may include an apparatus for separating constituent components of a fluid. This apparatus comprises a conduit configured to be received by a centrifuge rotor. The conduit has an inlet connected to an inlet line and an outlet fluidly coupled to a fluid chamber.

In another aspect, the invention includes a tubing set having a generally annularly configured channel, a plurality of lines, and a fluid chamber.

In another aspect the invention includes a fluid chamber for separating particle constituents from a liquid. The fluid chamber has at least one groove formed on an inner surface of a wall.

In another aspect, a fluid chamber includes at least one step formed on an inner surface of a wall.

In another aspect, the invention includes an apparatus having a holder for holding a fluid chamber on a rotor. Means are provided on the rotor for receiving a separation chamber capable of separating particles in response to centrifugal force.

In another aspect, the invention includes a method of separating white blood cells from a liquid by forming a substantial barrier to white blood cell flow through the fluid chamber, where the barrier includes a saturated fluidized bed of particles.

In an additional aspect, the invention includes a method of separating first particles from second particles by forming a saturated fluidized bed of third particles.

In another aspect of the invention, a method is provided for separating smaller first particles from larger second particles. This method includes the steps of adding third particles to a liquid having the first particles and second particles, the third particles being larger than the first particles and smaller than the second particles, and forming a saturated fluidized bed of at least one of the first and third particles.

In another aspect, the invention includes a fluid chamber connected to centrifugal generating means, means for establishing a saturated fluidized bed of particles within the fluid chamber and means for maintaining the saturated fluidized bed in the chamber.

In another aspect, the invention includes an apparatus having a fluid chamber, a separation chamber configured to be received by a centrifuge rotor to centrifugally separate particles within the separation chamber, and means for fluid coupling the fluid chamber to the separation chamber.

In another aspect, the invention includes a method of separating blood components. The method comprises the steps of applying a centrifugal force to blood to separate the blood into components including at least plasma, platelets, and white blood cells, whereby at least a portion of the platelets become activated during the applying step, and filtering the components to remove white blood cells, while a substantial number of platelets remain activated.

In another aspect the invention includes an apparatus and method for separating particles from a liquid by initially separating particles in a liquid according to different densities and/or different sedimentation velocities, flowing at least a portion of the particles separated in the initial separating step into a fluid chamber, and further separating the particles within the fluid chamber according to different sedimentation velocities.

In another aspect, the invention includes an apparatus and method for separating blood components by directing separated blood components from a separation chamber into a fluid chamber to filter the separated components.

In yet another aspect, the invention includes a method and apparatus for reducing Coriolis jetting and/or density inversion.

In a further aspect, the invention includes a method of separating particles without adding a substantial amount of a diluting fluid.

In yet another aspect, the invention includes an apparatus and method for separating and/or filtering blood components.

In particular the invention includes a method for continuously separating particles.

It is to be understood that both the foregoing general description and the following detailed description are exemplary, and are intended to provide further explanation of the invention as claimed. The accompanying drawings are included to provide a further understanding of the invention and are incorporated in and constitute a part of this specification. The drawings illustrate embodiments of the invention and, together with the description, serve to explain the principles of the invention.

BRIEF DESCRIPTION OF THE DRAWINGS

FIG. 13 illustrates a separation chamber and fluid chamber in another embodiment of the invention;

FIG. 14 is a partial view of a centrifuge apparatus including a separation chamber and multiple fluid chambers in a further embodiment of the invention;

FIG. 16 is a cross-sectional view of a fifth alternative embodiment of the fluid chamber of FIG. 2; and FIG. 17 is a cross-sectional view of a sixth alternative embodiment of the fluid chamber of FIG. 16.

DESCRIPTION OF THE PREFERRED EMBODIMENTS

Figure 1:
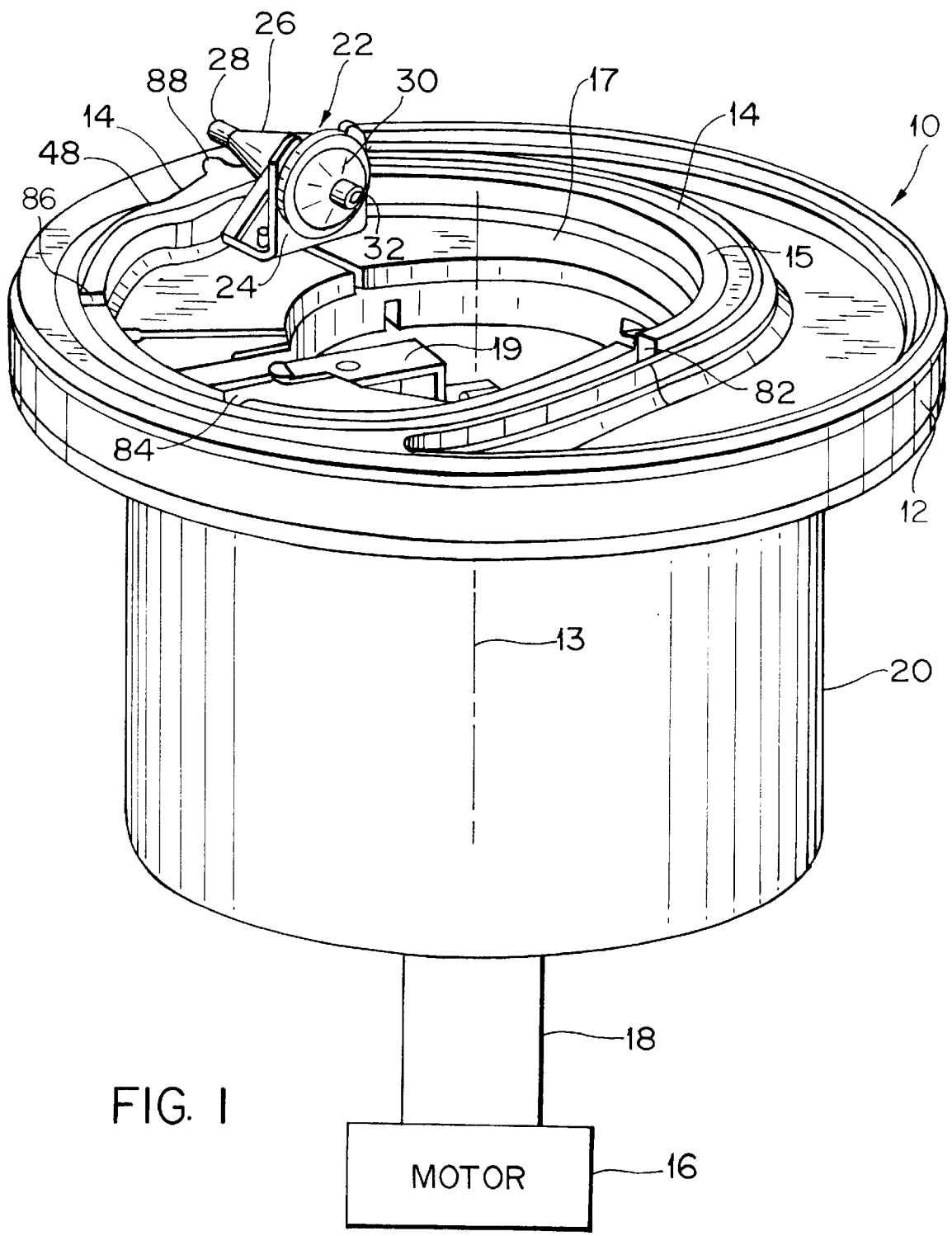
FIG. 1 is a perspective view of a centrifuge apparatus in accordance with a preferred embodiment of the invention.

Reference will now be made in detail to the present preferred embodiments of the invention illustrated in the accompanying drawings.

A preferred embodiment of the present invention is described by referring to its use with a COBE® SPECTRA™ two stage sealless blood component centrifuge manufactured by the assignee of the invention. The COBE® SPECTRA™ centrifuge incorporates a one-omega/two-omega sealless tubing connection as disclosed in U.S. Pat. No. 4,425,112 to Ito, the entire disclosure of which is incorporated herein by reference. The COBE® SPECTRA™ centrifuge also uses a two-stage blood component separation channel substantially as disclosed in U.S. Pat. No. 4,708,712 to Mulzet, the entire disclosure of which is also incorporated herein by reference. Although the preferred embodiment of the invention is described in combination with the COBE® SPECTRA™ centrifuge, this description is not intended to limit the invention in any sense.

As will be apparent to one having skill in the art, the present invention may be advantageously used in a variety of centrifuge devices commonly used to separate blood into its components. In particular, the present invention may be used with any centrifugal apparatus that employs a component collect line such as a platelet collect line or a platelet rich plasma line, whether or not the apparatus employs a two stage channel or a one-omega/two-omega sealless tubing connection.

In accordance with the invention there is provided an apparatus for filtering first particles from a liquid comprising a centrifuge rotor coupled to a motor for rotating the centrifuge rotor about an axis of rotation. As embodied herein and illustrated in FIG. 1, centrifuge 10 includes a rotor 12. The rotor 12 has an annular groove or passageway 14 having an open upper surface adapted to receive a conduit or channel 44 of a tubing set 70 shown in FIG. 4. The passageway 14 completely surrounds the rotor's axis of rotation 13 and is bounded on an inner surface by wall 15 positioned on a top surface 17 of rotor 12. A motor 16 is coupled to rotor 12 to rotate the rotor 12 about the axis of rotation 13. This coupling is accomplished directly or indirectly through a shaft 18 connected to an arm 19 that mounts to the rotor 12. Alternately, the shaft 18 may be coupled to the motor 16 through a gearing transmission (not shown). A shroud 20 is positioned on the rotor 12 to protect the motor 16 and shaft 18.

In accordance with the present invention, a holder is provided for holding a fluid chamber on the rotor with an outlet of the fluid chamber positioned closer to the axis of rotation than an inlet of the fluid chamber. As embodied herein and as illustrated in FIG. 1, the holder may include a mounting bracket 24 for maintaining a fluid chamber 22 on rotor 12 with an outlet 32 generally positioned closer to the rotation axis 13 than an inlet 28. The fluid chamber 22 fits within the mounting bracket 24 as illustrated in FIG. 1. The fluid chamber 22 may also be secured to the rotor 12 at alternate locations, such as beneath passageway 14. The fluid chamber 22 may be constructed of a transparent or translucent copolyester plastic, such as PETG, to allow viewing of the contents within the chamber interior with the aid of an optional strobe (not shown) during a centrifuge procedure.

Figure 2:
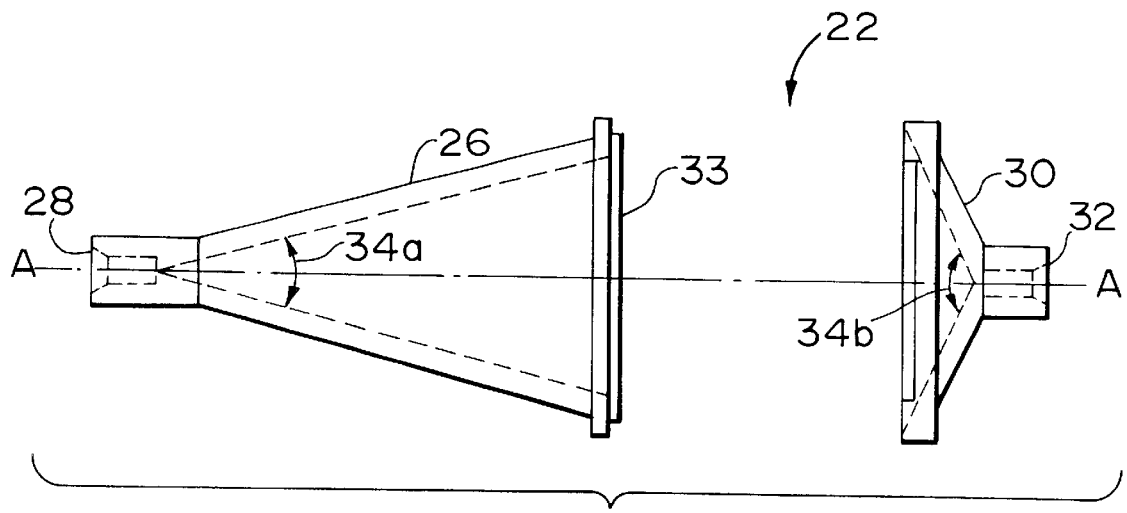
FIG. 2 is an exploded side view of a fluid chamber shown in FIG. 1.

As illustrated in FIG. 2, the fluid chamber 22 is formed by joining a first chamber section 26 having the inlet 28 to a second chamber section 30 having the outlet 32. The inlet 28 and outlet 32 are arranged along a longitudinal axis A—A.

In a preferred embodiment of the invention the fluid chamber 22 has an interior volume of about 14.5 ml., although this parameter may be increased or decreased depending on the particular application. The interior of the first chamber section 26 has a frustoconical shape with a conical angle 34a of approximately 30 degrees. The interior of the second chamber section 30 also has a frustoconical shape having a conical angle 34b of approximately 120 degrees. These angles may be varied. For example, the conical angle 34b may range from approximately 90 to 120 degrees and the conical angle 34a may range from approximately 30 to 90 degrees.

The volume of the fluid chamber 22 should be least large enough to accommodate enough platelets to provide a saturated fluidized particle bed (described below) for a particular range of flow rates, particle sizes, and centrifuge rotor 12 speeds.

Preferably, the fluid chamber interior has a maximum cross-sectional area 33 located at a position intermediate the inlet 28 and outlet 32 where sections 26, 30 join. The cross sectional area of the fluid chamber interior decreases or tapers from the maximum cross-sectional area 33 in both directions along axis A—A. Although the fluid chamber 22 is depicted with two sections 26, 30 having frustoconical interior shapes, the interior shapes may be paraboloidal, or of any other shape having a major cross-sectional area greater than the inlet or outlet area. The fluid chamber 22 may be constructed from a unitary piece of plastic rather than from separate sections.

Figure 3:
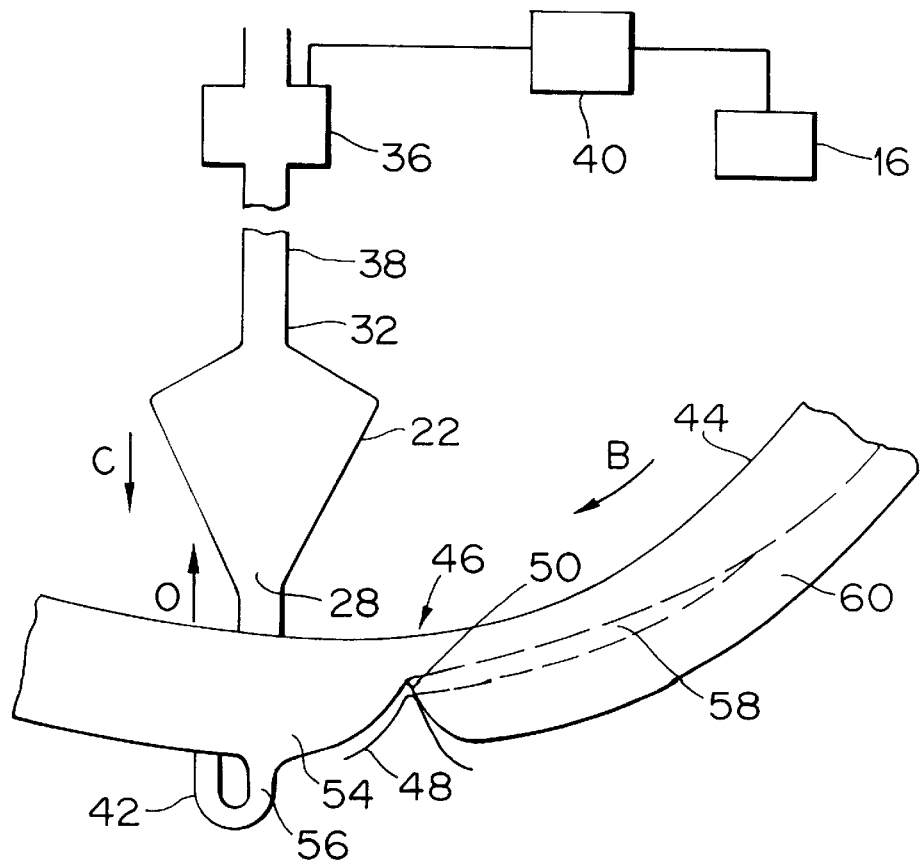
FIG. 3 is a partial schematic view of the apparatus of FIG. 1 illustrating a detailed view of components of the apparatus.

In accordance with the present invention, there is also provided means for supplying a substance to the inlet of the fluid chamber. As embodied herein and as schematically illustrated in FIG. 3, a pump 36 is fluidly connected to the fluid chamber 22 through outflow tubing 38. The pump 36 applies a vacuum force to the fluid chamber 22 for drawing fluid and particles into the fluid chamber 22 through the inlet 28. The pump 36 is preferably a peristaltic pump or impeller pump configured to prevent significant damage to blood components, but any fluid pumping or drawing device may be provided. In an alternative embodiment (not shown), the pump 36 may be fluidly connected to the inlet of the fluid chamber 22 to directly move substances into and through the fluid chamber 22. The pump 22 may be mounted at any convenient location.

In accordance with the invention there is also provided means for controlling the motor and/or the supply means to maintain a saturated fluidized bed of second particles within the fluid chamber and to cause first particles to be retained in the chamber. As embodied herein and illustrated in FIG. 3, the controlling means may include a controller 40 connected to both the centrifuge motor 16 and the pump 36. As explained in detail below, during a centrifuge operation, controller 40 maintains a saturated fluidized particle bed within the fluid chamber 22 to separate particles. Controller 40 may include a computer having programmed instructions provided by a ROM or RAM as is commonly known in the art.

The controller 40 may vary the rotational speed of the centrifuge rotor 12 by regulating frequency, current, or voltage of the electricity applied to the motor 16. Alternatively, the rotor speed can be varied by shifting the arrangement of a transmission (not shown), such as by changing gearing to alter a rotational coupling between the motor 16 and rotor 12. The controller 40 may receive input from a rotational speed detector (not shown) to constantly monitor the rotor speed.

The controller 40 may also regulate the pump 36 to vary the flow rate of the substance supplied to the fluid chamber 22. For example, the controller 40 may vary the electricity provided to the pump 36. Alternatively the controller 40 may vary the flow rate to the chamber 22 by regulating a valving structure (not shown) positioned either within an inflow tubing 42 connected to the inlet 28 or within outflow tubing 38. The controller 40 may receive an input from a flow detector (not shown) positioned within the inflow tubing 42 to monitor the flow rate of substances entering the fluid chamber 22. Although a single controller 40 having multiple operations is schematically depicted in the embodiment shown in FIG. 3, the control means of the invention may include any number of individual controllers, each for performing a single function or a number of functions. The controller 40 may control flow rates in many other ways as is known in the art.

Figure 4:
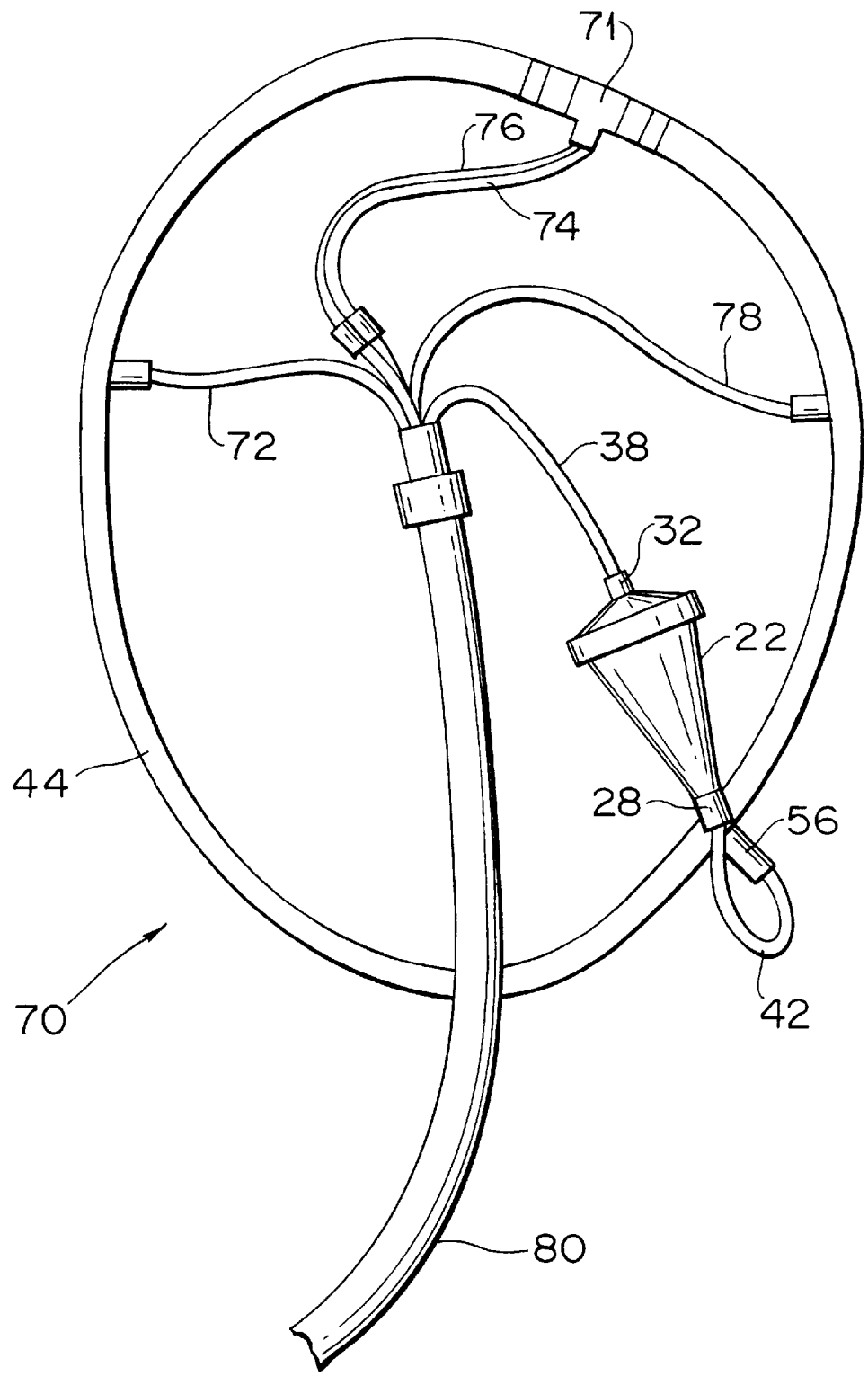
FIG. 4 depicts a portion of a tubing set in accordance with the invention.

As described above, the rotor 12 is configured with an annular passageway 14 that is open along a top surface as illustrated in FIG. 1. This passageway 14 is provided to receive a channel 44 of tubing set 70, as partially shown in FIG. 5. As best illustrated in FIG. 4, tubing set 70 preferably includes a semi-rigid conduit formed into a channel 44 having a generally rectangular cross-section. A connector 71 joins ends of the channel 44 to form an annular or loop shape that fits within passageway 14. A supply line 78 provides whole blood to an inlet of the semi-rigid channel 44, while a tubing segment 42, outlet lines 72, 74, and a control line 76 allow for removal of blood components during a centrifuge operation and flow control within the channel 44. Further details of the general configuration and functioning of the channel 44, tubing segment 42, and lines 72, 74, 76 and 78 are described in U.S. Pat. No. 4,708,712.

A protective sheath 80 surrounds the lines 72, 74, 76, 78 and outflow tubing 38. When the channel 44 of the tubing set 70 is removably positioned within the passageway 14, the lines 72, 74, 76 and 78 extend through slots 82, 84, 86, respectively, formed in wall 15, while the inflow tubing 42 rests in a slot 88 formed by passageway 14 (See FIGS. 1 and 5).

Figure 15:
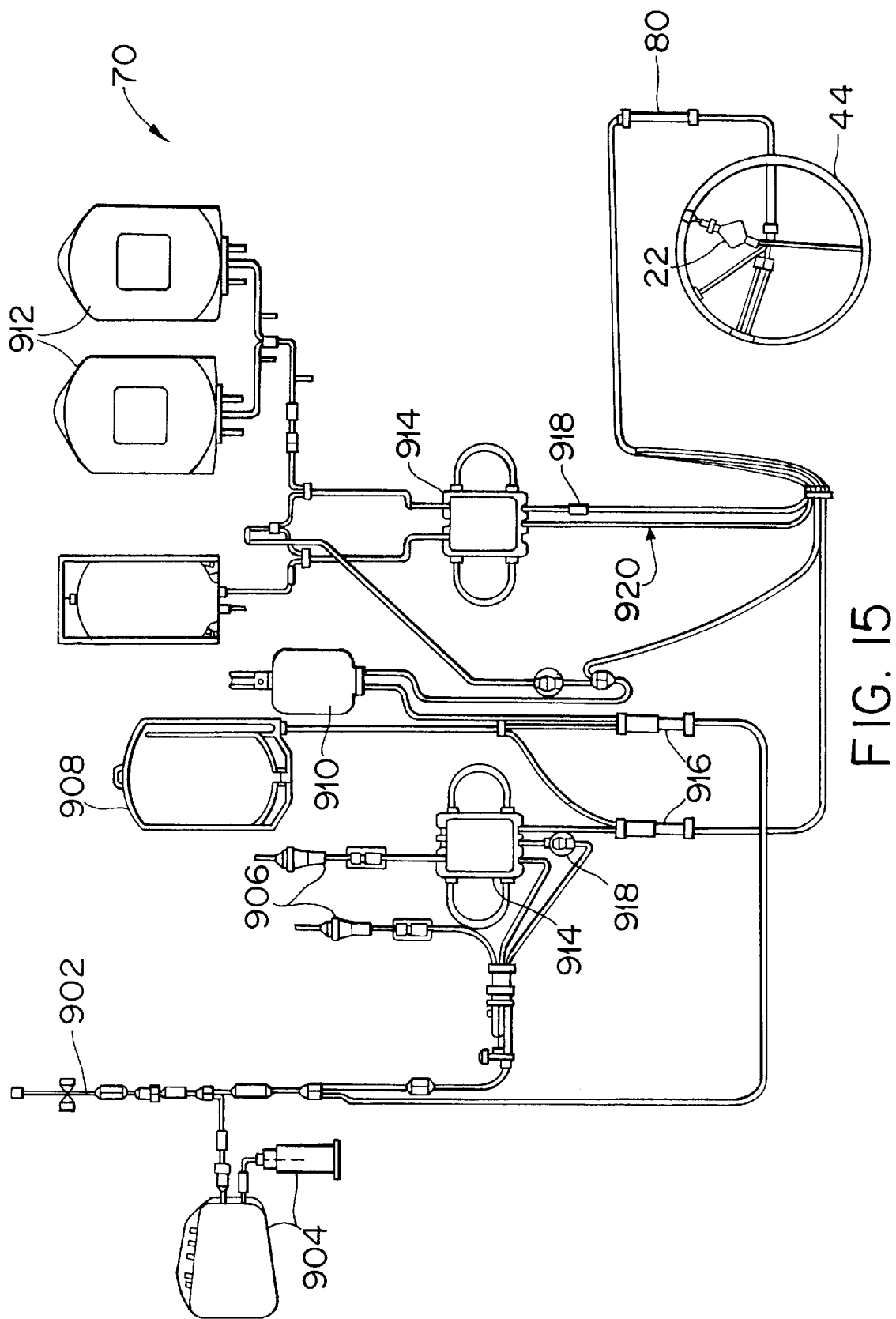
FIG. 15 is a schematic diagram illustrating a tubing set in accordance with the present invention, including the portion depicted in FIG. 4.

FIG. 15 is a more complete view of the tubing set 70. The tubing set 70 may further include a plurality of additional elements for collecting blood components including, but not limited to one or more donor access lines 902, sample devices 904, spikes 906, filled solution bags (not shown) for the addition of fluids to the tubing set 70, wastes bags 908, accumulator bags 910, blood component bags 912, pump cartridges 914 for interfitting with various fluid pumps such as the pump 36, air chambers 916, monitoring device interfaces 918, interconnecting tubing and fittings 920, and various miscellaneous elements and accessories.

Figure 5:
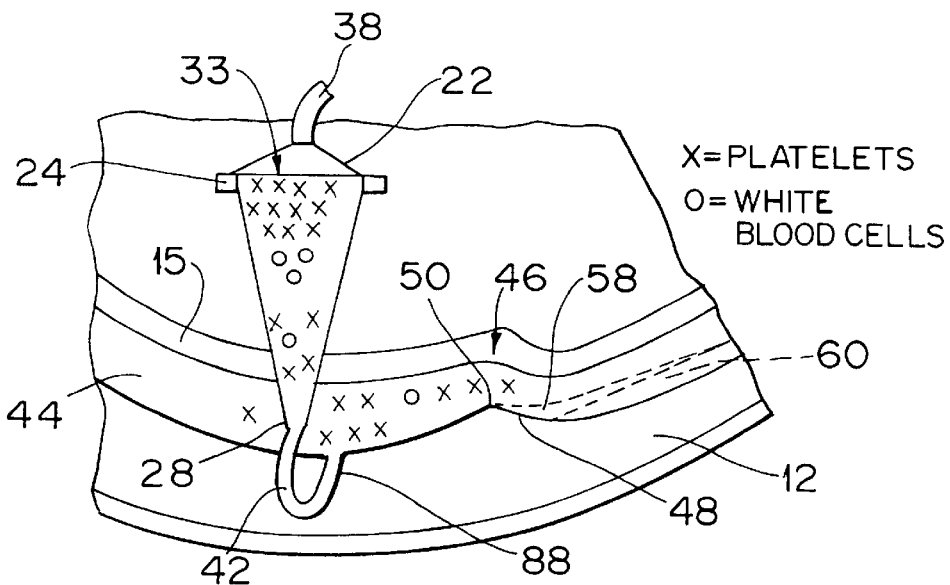
FIG. 5 schematically illustrates a saturated fluidized bed formed within a fluid chamber, where the fluid chamber is a component of the tubing set of FIG. 4 mounted to the centrifuge apparatus of FIG. 1.

As shown in FIGS. 3 and 5, a separation chamber 46 is positioned within a flow passage of the channel 44. Particles initially separate within the separation chamber 46 according to density and/or sedimentation velocity in response to centrifugal force. The separation chamber 46 includes a ridge 48 positioned on an outer wall of the passageway 14 for deforming a portion of the channel 44 to create a dam 50 within the channel 44. Alternatively, the dam 50 may be a permanent structure mounted within the flow passage of the channel 44. Although only a single separation chamber 46 and dam 50 are depicted in the figures, the flow passage may have multiple separation chambers or dams depending upon desired use.

When channel 44 is positioned in passageway 14, a collect well 54 forms in channel 44 adjacent dam 50. A tubing segment 42 connecting an outlet 56 of the well 54 to the inlet 28 of the fluid chamber 22 allows for separated substances in the collect well 54 to be conveyed to the fluid chamber 22. Although the preferred embodiment includes a tubing segment 42, any fluid coupling may be used between the separation chamber 46 and fluid chamber 22. For example, the inlet 28 of fluid chamber 22 may be directly connected to channel 44.

A method of separating particles of blood is discussed below with reference to FIGS. 3 and 5. Although the invention is described in connection with a blood component separation process, it should be understood that the invention in its broadest sense is not so limited. The invention may be used to separate a number of different particles. In addition the invention is applicable to both double needle and single needle blood purification or filtration applications. For example, the invention of the present application may be practiced with the SINGLE NEEDLE RECIRCULATION SYSTEM FOR HARVESTING BLOOD COMPONENTS of U.S. patent application Ser. No. 08/110,432, filed Aug. 23, 1993, U.S. Pat. No. 5,437,624, the disclosure of which is incorporated herein by reference.

Preferably the fluid chamber 22 is initially primed with a low density fluid medium, such as air, saline solution, or plasma, having a density less than or equal to the density of liquid plasma. This priming fluid allows for efficient establishment of a saturated fluidized bed of platelets within the fluid chamber 22. When a saline solution is used, this liquid enters the channel 44 through supply line 78. The saline then flows into the outlet 56 and through the chamber 22 when controller 40 activates pump 36. Controller 40 also initiates operation of the motor 16 to rotate the centrifuge rotor 12 and fluid chamber 22 in the direction of arrow "B" in FIG. 3. During rotation, twisting of fluid lines 72, 74, 76, 78 and outflow tubing 38 connected to the centrifuge rotor 12 and fluid chamber 22 is prevented by a sealless one-omega/two-omega tubing connection as is known in the art and described in U.S. Pat. No. 4,425,112.

After the apparatus is primed, and as the centrifuge rotates, whole blood or blood components are introduced through supply line 78 into the semi-rigid channel 44. When whole blood is used, the whole blood can be added to the semi-rigid channel 44 by transferring the blood directly from a donor through supply line 78. In the alternative, the blood may be transferred from a container, such as a blood bag, to supply line 78.

The blood within the channel 44 is subjected to a centrifugal force as the centrifuge rotor 12 continues to rotate in the direction of arrow "B" in FIG. 3. This centrifugal force acts in a radial direction away from the axis of rotation 13 of the rotor 12 as indicated by arrow "C" in FIG. 3.

The blood components undergo an initial separation within the channel 44. The components of whole blood stratify in order of decreasing density as follows: 1. red blood cells, 2. white blood cells, 3. platelets, and 4. plasma. The controller 40 regulates the rotational speed of the centrifuge rotor 12 to ensure that this particles stratification takes place. The blood particles form a buffy coat layer 58 and an outer layer 60 along an outer wall surface of the channel 44 within the separation chamber 46. The outer layer 60 includes particles having a density greater than the density of the particles in the buffy coat layer 58. Typically, the outer layer 60 includes red blood cells and white blood cells, while the buffy coat layer 58 includes platelets and white blood cells.

Plasma, the least dense blood component, flows within the channel 44 along the top surface of the buffy coat layer 58. When the height of the buffy coat layer 58 approaches the top of dam 50, the flowing plasma washes the platelets and some white blood cells of the buffy layer 58 over the dam 50. After these particles are washed over the dam 50, they enter the collect well 54. Some of the platelets may also flow past the collect well 54 and then reverse direction to settle back into the collect well 54, as described in U.S. patent application Ser. No. 08/422,598, entitled SPILLOVER COLLECTION OF SPARSE COMPONENTS SUCH AS MONONUCLEAR COMPONENTS OF WHOLE BLOOD, filed Apr. 14, 1995, U.S. Pat. No. 5,704,889, the disclosure of which is incorporated herein by reference.

The white blood cells and red blood cells within the outer layer 60 are removed through outlet line 74, while platelet poor plasma is removed through outlet line 72. The controller 40 may control optional pumps (not shown) connected to lines 72, 74, or 76 to remove these blood components, as is known in the art. After the red blood cells, white blood cells, and plasma are thus removed, they are collected and recombined with other blood components or further separated. Alternately, these removed blood components may be reinfused into a donor.

Plasma carries platelets and white blood cells from the collect well 54 into the fluid chamber 22, filled with the priming fluid, so that a saturated fluidized particle bed may be formed. The controller 40 maintains the rotation speed of the rotor 12 within a predetermined rotational speed range to facilitate formation of this saturated fluidized bed. In addition, the controller 40 regulates the pump 36 to convey plasma, platelets, and white blood cells at a predetermined flow rate through the tubing segment 42 and into inlet 28 of the fluid chamber 22. These flowing blood components displace the priming fluid from the fluid chamber 22.

When the platelet and white blood cell particles enter the fluid chamber 22, they are subjected to two opposing forces. Plasma flowing through the fluid chamber with the aid of pump 36 establishes a first viscous drag force when plasma flowing through the fluid chamber 22 urges the particles toward the outlet 32 in the direction "D", shown in FIG. 3. A second centrifugal force created by rotation of the rotor 12 and fluid chamber 22 acts in the direction "C" to urge the particles toward the inlet 28.

The controller 40 regulates the rotational speed of the rotor 12 and the flow rate of the pump 36 to collect platelets and white blood cells in the fluid chamber 22. As plasma flows through the fluid chamber 22, the flow velocity of the plasma decreases as the plasma flow approaches the maximum cross section area 33. This flow reaches a minimum velocity at this maximum section area 33. Because the rotating centrifuge rotor 12 creates a sufficient gravitational field in the fluid chamber 22, the platelets accumulate near the maximum cross-sectional area 33 rather than flowing from the fluid chamber 22 with the plasma. The white blood cells accumulate somewhat below the maximum cross section area 33. However, density inversion tends to mix these particles slightly during this initial establishment of the saturated fluidized particle bed.

The larger white blood cells accumulate slightly closer to inlet 28 than the smaller platelet cells, because of their different sedimentation velocities. Preferably, the rotational speed and flow rate are controlled so that very few platelets and white blood cells flow from the fluid chamber 22 during formation of the saturated fluidized particle bed.

The platelets and white blood cells continue to accumulate in the fluid chamber 22 while plasma flows through the fluid chamber 22. As the concentration of platelets increases, the interstices between the particles become reduced and the viscous drag force from the plasma flow gradually increases. Eventually the platelet bed becomes a saturated fluidized particle bed within the fluid chamber 22. Since the bed is now saturated with platelets, for each new platelet that enters the saturated bed in the fluid chamber 22, a single platelet must exit the bed. Thus, the bed operates at a steady state condition with platelets exiting the bed at a rate equal to the rate additional platelets enter the bed after flowing through inlet 28. This bed is depicted schematically in FIG. 5, where the "X" symbol represents platelets and the "O" symbol represents white blood cells. As explained below, and depicted in FIG. 5, the saturated fluidized particle bed substantially obstructs or prevents white blood cells, "O", from passing through the fluid chamber 22.

The saturated bed establishes itself automatically, independent of both the concentration of particles flowing into the fluid chamber 22 and the flow rate of liquid entering fluid chamber 22. Plasma flowing into the fluid chamber 22 passes through the platelet bed both before and after the platelet saturation point.

The saturated bed of platelets occupies a varying volume in the fluid chamber 22 near the maximum cross sectional area 33, depending on the flow rate and centrifugal field. The number of platelets in the saturated bed depends on a number of factors, such as the flow rate into the fluid chamber 22, the volume of the fluid chamber 22 and rotational speed. If these variables remain constant, the number of platelets in the saturated fluidized bed remains substantially constant. When the flow rate of blood components into the fluid chamber 22 changes, the bed self adjusts to maintain itself by either releasing excess platelets or accepting additional platelets flowing into the fluid chamber 22. For example, when the plasma flow rate into the fluid chamber 22 increases, this additional plasma flow sweeps excess platelets out of the now super-saturated bed, and the bed reestablishes itself in the saturated condition at the increased flow rate. Therefore, the concentration of platelets in the bed is lower due to the release of bed platelets.

After the saturated fluidized bed of platelets forms, flowing plasma carries additional platelets into the fluid chamber 22 and the bed. These additional platelets add to the bed and increase the viscous drag of the plasma flow through the bed. At some point the viscous drag is sufficient to cause platelets near the maximum cross-section area 33 to exit the saturated bed and fluid chamber 22. Thus, if the rotational speed and flow rate into the fluid chamber 22 remain constant, the number and concentration of platelets flowing into the saturated fluidized bed of platelets substantially equals the number and concentration of platelets released from the bed. This is in sharp contrast from the prior art.

Although the bed is saturated with platelets, a small number of white blood cells may be interspersed in the platelet bed.

These white blood cells, however will tend to "fall" or settle out of the platelet bed toward inlet 28. Most white blood cells generally collect within the fluid chamber 22 between the saturated platelet bed and the inlet 28, as depicted in FIG. 5 and described below.

The saturated fluidized bed of platelet particles functions as a filter or barrier to white blood cells flowing into the fluid chamber 22. When blood components flow into the fluid chamber 22, plasma freely passes through the bed. However, the saturated fluidized platelet bed creates a substantial barrier to white blood cells entering the fluid chamber 22 and retains these white blood cells with in the fluid chamber 22. Thus, the bed effectively filters white blood cells from the blood components continuously entering the fluid chamber 22, while allowing plasma and platelets released from the saturated bed to exit the chamber 22. This replenishment and release of platelets is referred to as the bed's self-selecting quality. Substantially all of these filtered white blood cells accumulate within the fluid chamber 22 between the saturated fluidized platelet bed and the inlet 28.

The particle separation or filtration of the saturated fluidized particle bed obviates a number of limitations associated with prior art elutriation. For example, particles may be separated or filtered in a continuous steady state manner without batch processing. In addition, an additional elutriating fluid medium is not required. Furthermore, after the saturated fluidized particle bed is established, flow rates may be varied without changing the size of the particles leaving the fluid chamber 22. Unlike prior art elutriation, the present invention establishes a saturated particle bed consisting of numerically predominant particles. This bed automatically passes the predominant particles while rejecting larger particles.

The apparatus and method of the invention separate substantially all of the white blood cells from the platelets and plasma flowing through the fluid chamber 22. The barrier to white blood cells is created, at least in part, because white blood cells have a size and sedimentation velocity greater than that of the platelets forming the saturated fluidized particle bed. Therefore, particles of similar densities are separated according to different sizes or sedimentation velocities.

Because the initial separation at dam 50 and the saturated fluidized bed remove a majority of the red blood cells and white blood cells, the fluid exiting the fluid chamber 22 consists mainly of plasma and platelets. A device as described herein was operated 30 times using whole human blood. Each operation resulted in a leukopoor product having less than $3 \times 10^6$ white blood cells per $3 \times 10^{11}$ platelets. Based on these results it is expected that platelet product exiting the fluid chamber 22 will consistently (at least 99% of the time) meet the leukopoor standard of less than $5 \times 10^6$ white blood cells when at least $3 \times 10^{11}$ platelets flow from the fluid chamber 22.

Unlike a conventional porous filter, where the filtered white blood cells are retained in the filter, the present invention allows a substantial fraction of white blood cells to be recovered and returned to the donor.

Preferably, 80% to 99% of the platelets initially entering the channel 44 may be recovered in a viable state. More preferably, at least 95% or at least 98% of the platelets initially entering the channel 44 are recovered from both the channel 44 and the fluid chamber 22.

When the blood components are initially separated with the separation chamber 46, a substantial number of platelets may become slightly activated. The saturated fluidized platelet bed allows white blood cells to be filtered from plasma and platelets despite this slight activation. Thus, the present invention does not require a waiting period to filter white blood cells after blood components undergo initial separation in a separation chamber 46. This is in contrast to methods using conventional filters.

After separation, the platelets and plasma exiting the fluid chamber 22 are collected in appropriate containers and stored for later use. The red blood cells and white blood cells removed from the semi-rigid channel 44 may be combined with the remainder of the plasma in the system for donor reinfusion or storage. Alternatively, these components may be further separated by the apparatus 10.

In a preferred embodiment of the invention, the controller 40 regulates the rotational speed of the rotor 12 within a preferred range of 1,800 to 2,400 RPM. Preferably the rotation is controlled at 2,400 RPM to create a gravitational field within the fluid chamber 22 ranging from approximately 800 G adjacent to the inlet 28 to approximately 500 G adjacent to the outlet 32. The controller 40 maintains the flow rate into the fluid chamber 22 within a range of 1 ml/min to 15 ml/min. The preferred flow rate ranges from 2 ml/min to 8 ml/min. The specific flow rate is selected according to an initial platelet count and the total volume of whole blood being processed, among other things.

In a preferred embodiment, filtering may take place at the same flow rate used to form the saturated fluidized bed. Optionally the flow rate during filtering may be greater than the flow rate used during the bed formation to increase the rate of particle filtration. For this optional arrangement, the controller 40 may increase the flow rate of the blood components entering the fluid chamber 22 while maintaining the saturated fluidized bed. The controller 40 increases flow rate by increasing the rate of pump 36.

The controller 40 maintains the saturated fluidized bed throughout the filtering process as blood components flow into the fluid chamber 22. The controller 40 ensures that the flow through the fluid chamber 22 is smooth and steady by regulating the supply of fluid and rotation of the centrifuge rotor 12. This regulation properly balances the forces in the fluid chamber 22 to maintain the saturated fluidized bed. As described in more detail below, the controller 40 may increase flow into the fluid chamber 22 while maintaining the saturated fluidized bed.

At the end of a blood component separation session, the controller 40 may recover platelets retained both in the buffy coat layer 58 of channel 44 and within the saturated fluidized bed of fluid chamber 22. The controller 40 recovers platelets in the buffy coat layer 58 by either decreasing rotational speed of the rotor 12 or increasing the amount of plasma exiting the channel 44. For example, in a preferred manner of recovering platelets in the buffy coat layer, the rotor speed is suddenly decreased from 2,400 RPM to 1,800 RPM, and then increased back to 2,400 RPM. This spills platelets and white blood cells retained in the buffy coat layer 58 over the dam 50 and into the fluid chamber 22. Within the fluid chamber 22 the saturated fluidized platelet bed blocks passage of the white blood cells from the buffy coat layer 58, while buffy coat layer 58 platelets simultaneously add to the bed and release platelets from the saturated bed. Thus, the apparatus may filter substantially all of the white blood cells from the buffy coat layer 58. This increases platelet yield significantly.

The buffy coat layer 58 may spill over the dam in the manner described in above-mentioned U.S. patent application Ser. No. 08/422,598, U.S. Pat. No. 5,704,8896. This is particularly effective in a mononuclear cell collection procedure, because the fluid chamber 22 may allow for separation of red blood cells from mononuclear cells.

In addition, platelets in the saturated fluidized bed are harvested to recover a substantial number of platelets from the fluid chamber 22. During bed harvest, the controller 40 increases the flow rate and/or decreases the centrifuge rotator 12 speed to release platelets from the bed. This flushes from the fluid chamber 22 most of the platelets that made up the saturated fluidized bed to substantially increase platelet yield. The harvesting continues until substantially all of the platelets are removed, just before an unacceptable number of white blood cells begin to flow from the fluid chamber 22.

The harvested platelets that made up the bed may be combined with the platelets previously collected. In addition, the remainder of contents of the fluid chamber 22, having a high concentration of white blood cells, can be separately collected for later use or recombined with the blood components removed from channel 44 for return to a donor.

The invention particularly allows trace or contaminating first particles to be separated from a liquid having a larger number of second particles. Preferably the first particles to be filtered, such as white blood cells, have a concentration insufficient to form a saturated fluidized particle bed. However, the invention in its broadest application is directed to either separating first particles from liquid or separating first from second particles without concern for particular particle concentrations.

Although the inventive device and method have been described in terms of removing white blood cells and collecting platelets, this description is not to be construed as a limitation on the scope of the invention. The invention may be used to separate any of the particle components of blood from one another. For example, the saturated fluidized bed may be formed from red blood cells to prevent flow of white blood cells through the fluid chamber 22, so long as the red blood cells do not rouleau (clump). Alternatively, the liquid for carrying the particles may be saline or another substitute for plasma. In addition, the invention may be practiced to remove white blood cells or other components from whole blood removed from an umbilical cord to collect stem cells. Further, one could practice the invention by filtering or separating particles from fluids unrelated to either blood or biologically related substances.

The apparatus and method of the invention may separate white blood cells, including stem cells, and tumor cells by forming a saturated fluidized particle bed of stem cells to substantially prevent tumor cells from flowing through the fluid chamber 22. In the alternative, the tumor cells may form a saturated fluidized particle bed to substantially obstruct flow of stem cells through the fluid chamber 22.

In another aspect of the invention, smaller first particles, such as tumor cells, may be separated from larger second particles, such as stem cells, by forming a saturated fluidized particle bed with intermediate sized third particles. Initially, intermediate sized third particles are added to a liquid carrying the first and second particles. Preferably, the concentration of added third particles exceeds the concentration of both the first and second particles. These third particles are preferably magnetic micro-beads or some other substance readily separable from the other particles.

The liquid carrying the first, second, and third particles then passes into the fluid chamber 22. Eventually, the third particles form a saturated fluidized particle bed, in the same manner as described above. As more of the liquid and particles flow into the fluid chamber 22, the liquid and smaller first particles pass through the saturated third particle bed, while the bed obstructs movement of the second particles through the bed. Thus, the first and second particles separate within the fluid chamber 22.

The saturated fluidized bed may release third particles as more third particles flow into the bed or when flow rate into the fluid chamber 22 changes. These third particles may be removed from the liquid and first particles exiting the fluid chamber 22. In a preferred embodiment, a particle remover (not shown) having a magnet, magnetically attracts magnetic third particles to remove them from the liquid. Thus, a substantially purified concentration of first particles is obtained.

This alternate method is useful to separate first and second particles both being present in low concentrations and having similar densities, but different sizes. Although the third particles for forming the bed are preferably added along with the first and second particles, they may also be introduced into the fluid chamber 22 in separate steps. This aspect of the invention may be particularly useful in separating tumor cells from stem cells or other blood components, as mentioned above. Alternatively, the first particles may be tumor cells and the second particles may be stem cells. However, this variant of the inventive method may be practiced to separate many different types of particles. For example, tumor cells can be separated from stem cells so as to reduce graft versus host disease after stem cell transfusion.

Additional embodiments of the invention will now be described where like or similar elements are identified throughout the drawings by reference characters having the same final two digits.

Figures 6, 7:
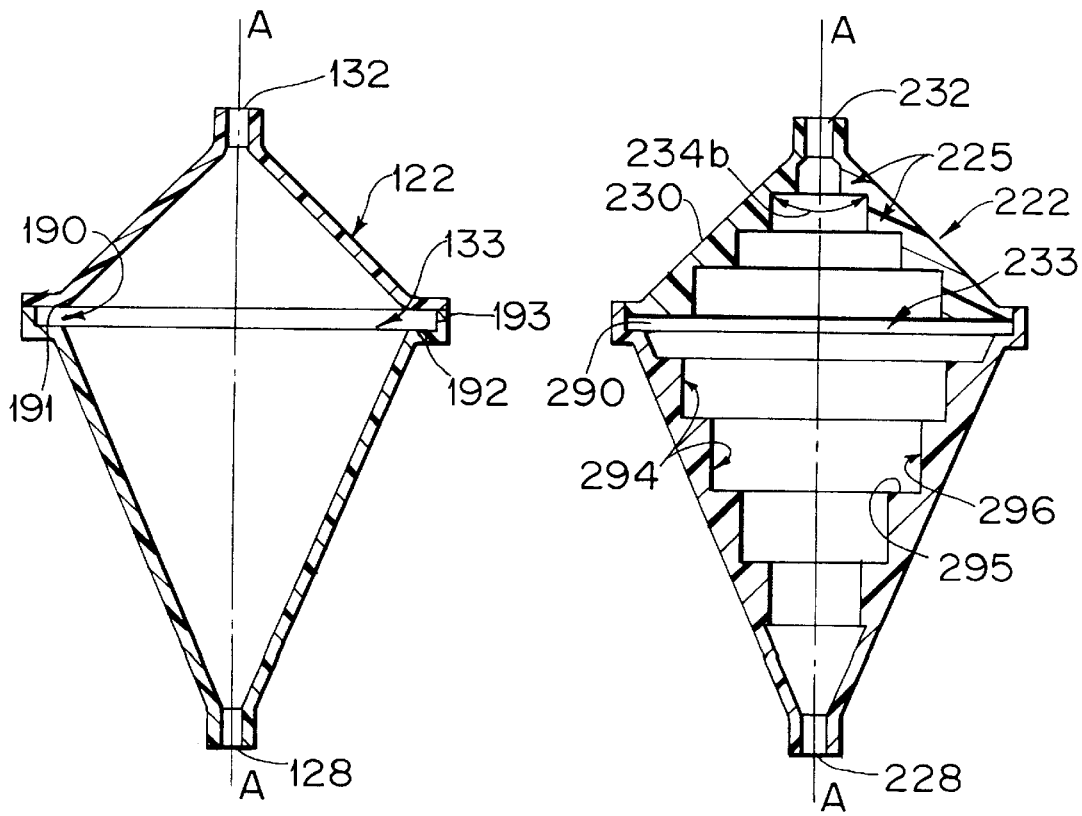
FIG. 6 is a cross-sectional view of a first alternate embodiment of the fluid chamber of FIG. 2.
FIG. 7 is a cross-sectional view of a second alternative embodiment of the fluid chamber of FIG. 2.

As shown in FIG. 6, another embodiment of the invention includes a fluid chamber 122 having an inlet 128 and an outlet 132. A groove 190 is formed on an inner surface of the fluid chamber 122 at a position of the maximum cross-sectional area 133. Top and bottom portions 191, 192, oriented substantially perpendicular to a longitudinal axis A—A of the fluid chamber 122, are joined by a side 193. Preferably, the side 193 is parallel to the axis A—A and surrounds this axis to form the substantially annular groove 190.

In a preferred embodiment the side 193 is 0.1 inches, while the top and bottom portions 191, 192 are each 0.08 inches. However, the groove 190 may be configured in many different shapes and sizes without departing from the invention.

The groove 190 helps to disperse Coriolis jetting within the fluid chamber 122. Thus, groove 190 improves the particle barrier capability of the saturated fluidized particle bed. Sudden increases in liquid flow rate during a particle separation procedure may limit the ability of the saturated fluidized particle bed to obstruct particle passage. Liquid flowing into the fluid chamber 22 undergoes a Coriolis jetting effect. This jetting flow reduces the filtration effectiveness of the saturated fluidized particle bed because liquid and particles may pass between the saturated fluidized particle bed and an interior wall surface of the fluid chamber 22 rather than into the bed itself. The fluid chamber 122 including groove 190 counteracts these effects by channeling Coriolis jetting flow in a circumferential direction partially around the axis A—A of fluid chamber 122. Therefore, the groove 190 improves the particle obstruction capability of the saturated bed, especially when liquid flow rates increase.

FIGS. 16 and 17 depict fluid chambers 1022 and 1022', respectively, having alternate embodiments of grooves 1090, 1090'. As illustrated in FIG. 16, fluid chamber 1022 includes a groove 1090 having a side 1093 and top and bottom portions 1091 and 1092 formed circumferentially on the inner surface of the fluid chamber 1022 at a position of a maximum cross-sectional area 1033. These top and bottom portions 1091 and 1092 may be perpendicular to a longitudinal axis A—A, while the side 1093 may be parallel to the axis A—A to form a substantially annular groove 1090.

As shown in FIG. 16, a circumferential lip 1094, located closer to the axis A—A than the side 1093, extends from the top portion 1091. The bottom portion 1092 and lip 1094 define a groove entrance 1096. As shown in FIG. 16, this groove entrance 1096 may completely surround axis A—A.

Alternatively, as shown in FIG. 17, the groove entrance may include a plurality of slot-shaped entrances 1095' spaced about the circumference of the fluid chamber 1022' at the position of maximum cross-sectional area 1033'. In this embodiment, the lip 10941 extends to the bottom portion 1092' to form an inner groove wall 1097' located between the slot-shaped entrances 1095.

Preferably, a first entrance 1095' may be provided at a location corresponding to the location of Coriolis jetting, and a second entrance (not shown) may be provided at a diametrically opposite location. The Coriolis jet flow enters the groove 1090' at a first slot-shaped entrance 1095', travels circumferentially around the groove 1090' in both clockwise and counter-clockwise directions, and then exits at another slot-shaped opening.

The configurations of FIGS. 16 and 17 are believed to improve direction of Coriolis jetting momentum and further improve performance. The groove configurations of FIGS. 16 and 17 may be optionally employed in conjunction with any of the fluid chamber embodiments described herein.

FIG. 7 depicts another embodiment of a fluid chamber 222. A plurality of steps 294 are formed on an inner surface of the fluid chamber 222 between the position of the maximum cross section 233 and the inlet 228. Although only four steps 294 are illustrated, any number of steps 294 may be provided in the fluid chamber 222.

Each step 294 has a base surface 295 oriented substantially perpendicular to a longitudinal fluid chamber axis A—A. In addition, a side surface 296 is positioned orthogonal to the base surface 295. Although FIG. 7 depicts a corner where side surface 295 and base surface 295 intersect, a concave groove may replace this corner. In a preferred embodiment each step 294 surrounds the axis A—A to bound a cylindrical shaped area. Further, the fluid chamber 222 optionally includes a groove 290.

The base surface 295 is 0.05 inches and the side surface 296 is 0.02 inches in a preferred embodiment. However, the sizes for these surfaces and the configuration of each step 294 may be modified without departing from the scope or spirit of the invention.

Adding steps 294 to the fluid chamber 222, also improves the particle obstruction characteristics of the saturated fluidized particles bed, in particular during increases in the rate of fluid flow. The steps 294 provide this improvement by providing momentum deflecting and redirecting surfaces to reduce Coriolis jetting in fluid chamber 222. When Coriolis jetting takes place, the liquid and particles of the jet travel along an interior surface of the fluid chamber 222 that faces the direction of centrifuge rotation. Therefore, the jet may transport particles between the fluid chamber interior surface and either a saturated fluidized particle bed or an elutriation field positioned in the fluid chamber 222. Thus, particles traveling in the jet may exit the fluid chamber 222 without being separated.

Steps 294 direct or alter the momentum of the Coriolis jet flow of liquid and particles generally in a circumferential direction about axis A—A. Thus, a substantially number of particles originally flowing in the jet must enter the saturated fluidized bed or elutriation field to be separated.

As shown in FIG. 7, the fluid chamber 222 may include additional steps 225 shaped similar to steps 294. The additional steps 225 are located between the position of the maximum cross-section 233 and a fluid chamber outlet 232. In a fashion similar to that described above, these steps 225 tend to redirect the Coriolis jet flow in a circumferential direction surrounding axis A—A.

In addition to adding steps 294 and 225, the conical angle 234*b* of the second chamber section 230 may be decreased from 120° to 45° to reduce particle contamination caused by density inversion. If faster sedimenting particles should migrate past the maximum cross section 233, the smaller angled walls partially limit some of these particles from flowing directly to outlet 232 because density inversion does not exist in the section 230. Thus, the faster sedimenting particles will "fall" or migrate back between area 233 and inlet 228 under the influence of the gravity centrifugal field, rather than flowing from outlet 232. Optionally, any of the fluid chambers disclosed herein may include a second chamber section 230 with a conical angle 234b less than 120°.

Figure 8:
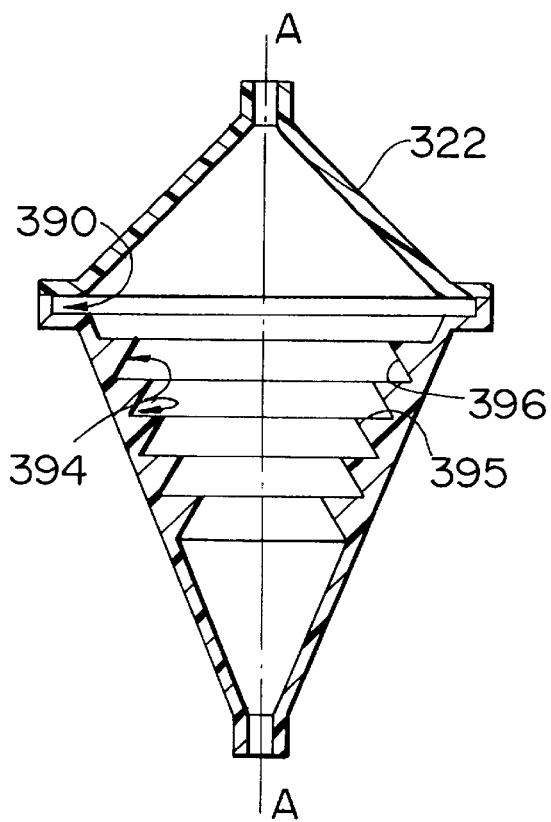
FIG. 8 is a cross-sectional view of a third alternative embodiment of the fluid chamber of FIG. 2.

FIG. 8 illustrates an additional embodiment of a fluid chamber 322 having steps 394 and an optional groove 390 similar to groove 190. As shown in FIG. 8, each step 394 includes a base surface 395 substantially perpendicular to axis A—A. This embodiment also includes a side surface 396 oriented at an acute angle to the base surface 395.

Figure 9:
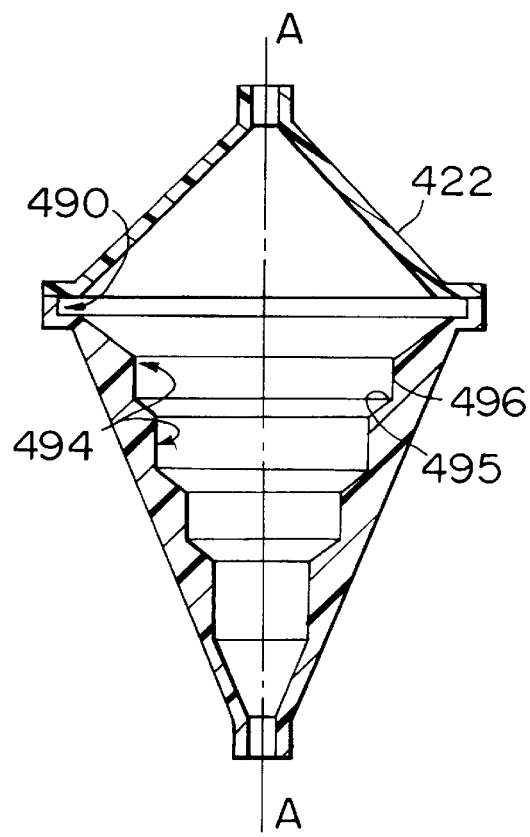
FIG. 9 is a cross-sectional view of a fourth alternative embodiment of the fluid chamber of FIG. 2.

In FIG. 9 a further embodiment of a fluid chamber 422 including flow limiting steps 494 and an optional groove 490 is depicted. A side surface 496 of each step 494 is substantially parallel to an axis A—A and forms an obtuse angle with base surface 495.

In FIGS. 6–9, the grooves 190, 290, 390, 490 and steps 294, 394, 494 may either completely or only partially surround the chamber axis A—A. These features are provided to facilitate fluid flow rate increases, as described below, as well as to improve steady state performance of the fluid chamber. During blood component separation, the grooves 190, 290, 390, 490 and steps 294, 394, 494 greatly reduce the number of white blood cells that would otherwise bypass the saturated fluidized platelet bed.

The grooves 190, 290, 390, 490, steps 294, 394, 494, and additional steps 225 may be formed in many different configurations without departing from the scope, or spirit of the invention. For example, the base surface and/or side surface of one or more of the steps 294, 394, 494 may have a concave shape. In addition the steps 294, 394, 494 may be arranged in a spiral surrounding axis A—A. Further, a portion of the base surface 295, 395, 495 extending around axis A—A may be positioned lower than a remainder of this surface to form a concavity.

Although the fluid chambers 122, 222, 322, 422, 1022, 1022' are described for use in forming a saturated fluidized particle bed, this description is not intended to limit the scope of the invention in its broadest sense. Because particle separation difficulties, such as those discussed in Sartory, may be reduced or eliminated, a significant advancement from the prior art has been made. These fluid chambers 122, 222, 322, 422 may be used in any particle separation process. In particular, a fluid chamber having a channel, step, or additional step may be used in elutriation.

The grooves 190, 290, 390, 490, steps 294, 394, 494, and additional step 225 may be formed in an injection molding process. Preferably, the fluid chambers 22, 122, 222, 322, 422, 1022, 1022' are initially formed by injection molding in multiple pieces, preferably two, and bonded together by any of several well known processes, such as RF welding, ultrasonic welding, hot plate welding, solvent bonding, or adhesive bonding. Alternatively, these fluid chambers may be formed from a unitary plastic material, as by blow molding. However, any known manufacturing process may be practiced to fabricate the chambers.

When one of the fluid chambers 122, 222, 322, 422, 1022, 1022' is substituted for the fluid chamber 22, the controller 40 may regulate flow of the liquid having first particles in number of preferred ways. Because these fluid chamber designs reduce Coriolis jetting and/or density inversion, the controller 40 may increase flow rate without disrupting the saturated fluidized particle bed.

While maintaining rotational speed of the rotor 12 at a substantially constant rate, the controller 40 may increase flow through the fluid chamber 122, 222, 322, 422, 1022, 1022' with one of, or a combination of, the following different routines. In one routine the controller 40 increases flow rate by rapidly or instantaneously increasing flow through the fluid chamber 122, 222, 322, 422, 1022, 1022'. In another routine flow rate is increased gradually over time. In yet a further routine, the controller 40 increases flow rate in a sequential manner by gradually increasing the flow rate, maintaining this increased flow rate, and then gradually increasing flow rate again.

However, if the apparatus 10 includes the fluid chamber 22, shown in FIGS. 1–5, the flow rate control may be more limited. The flow velocity of the liquid and particles entering the fluid chamber 22 should not undergo rapid or extreme fluctuation, otherwise temporary disruption of the effectiveness of the bed may result. The flow velocity can drop suddenly without affecting the bed, however sudden increases in velocity, if large enough, may disrupt the bed to allow particles, such as white blood cells, to exit the fluid chamber 22.

The controller 40 increases flow into the fluid chamber 22 while maintaining the saturated fluidized bed. The controller 40 may perform this flow rate increase by gradually increasing flow in a continuous fashion until a final flow rate is achieved. In a preferred embodiment, including the fluid chamber 22 shown in FIG. 2, the controller 40 increases the flow rate into the fluid chamber 22 by a ratcheting process.

The controller 40 maintains the bed and increases the flow rate in the ratcheting process by initially reducing the rotational speed of the rotor 12. However, the rotational speed of the rotor 12 is not reduced to a level that allows red blood cells in outer layer 60 to spill over dam 50, otherwise a significant number of both red blood cells and white blood cells will flow into the fluid chamber 22. In the preferred embodiment of the invention, the controller 40 lowers the rotational speed of the rotor 12 so that a centrifugal force at dam 50 remains above 850 G. Then, the controller calculates a value for $K=Q_i/N_i^2$, where K is a constant, $Q_i$ is the current flow rate into the fluid chamber 22, and $N_i$ is the current rotational speed of the centrifuge rotor 12.

After the controller 40 reduces the rotational speed of the rotor 12 and calculates K, the controller 40 simultaneously increases both the flow rate into the fluid chamber 22 and the rotational speed of the rotor 12. Thus, an increasing centrifugal force in the fluid chamber 22 counteracts with increasing fluid flow forces in the fluid chamber 22 to maintain the saturated fluidized particle bed as a barrier to other particles. The new flow rate into the chamber, Q, and the new rotational speed N satisfy the equation: $Q/N^2=K$. Therefore, $Q/N^2$ equals $Q_i/N_i^2$.

To increase the flow rate even further, the controller 40 may continue to simultaneously increase both flow rate and rotational speed. Also, if necessary, the controller 40 may repeat the ratcheting process to further increase flow rate. This is accomplished by repeating the steps of reducing rotational speed and simultaneously increasing both flow rate and rotational speed.

In addition, the controller 40 preferably returns the saturated fluidized particle bed to its original state if a pause in fluid flow to the fluid chamber 22 causes the bed to collapse. The controller 40 may constantly monitor both flow rate, Q, and rotational speed, N, to calculate a value for $K=Q/N^2$. If the flow into the fluid chamber 22 momentarily pauses to collapse the saturated fluidized bed, the particles that made up the bed temporarily remain in the fluid chamber 22. When fluid flow to the fluid chamber 22 is reinitiated, the controller 40 controls both the flow rate, Q, and rotational speed, N, so that these parameters satisfy the $K=Q/N^2$ relationship existing immediately before fluid flow to the fluid chamber 22 was interrupted. This automatically returns the particles of the collapsed bed back into a saturated fluidized bed form.

After a bed collapses the saturated fluidized particle bed may recover in many other different ways. For example, after a pause in fluid flow the flow rate may be increased in a stepwise or gradual fashion to provide bed recovery.

Figure 10:
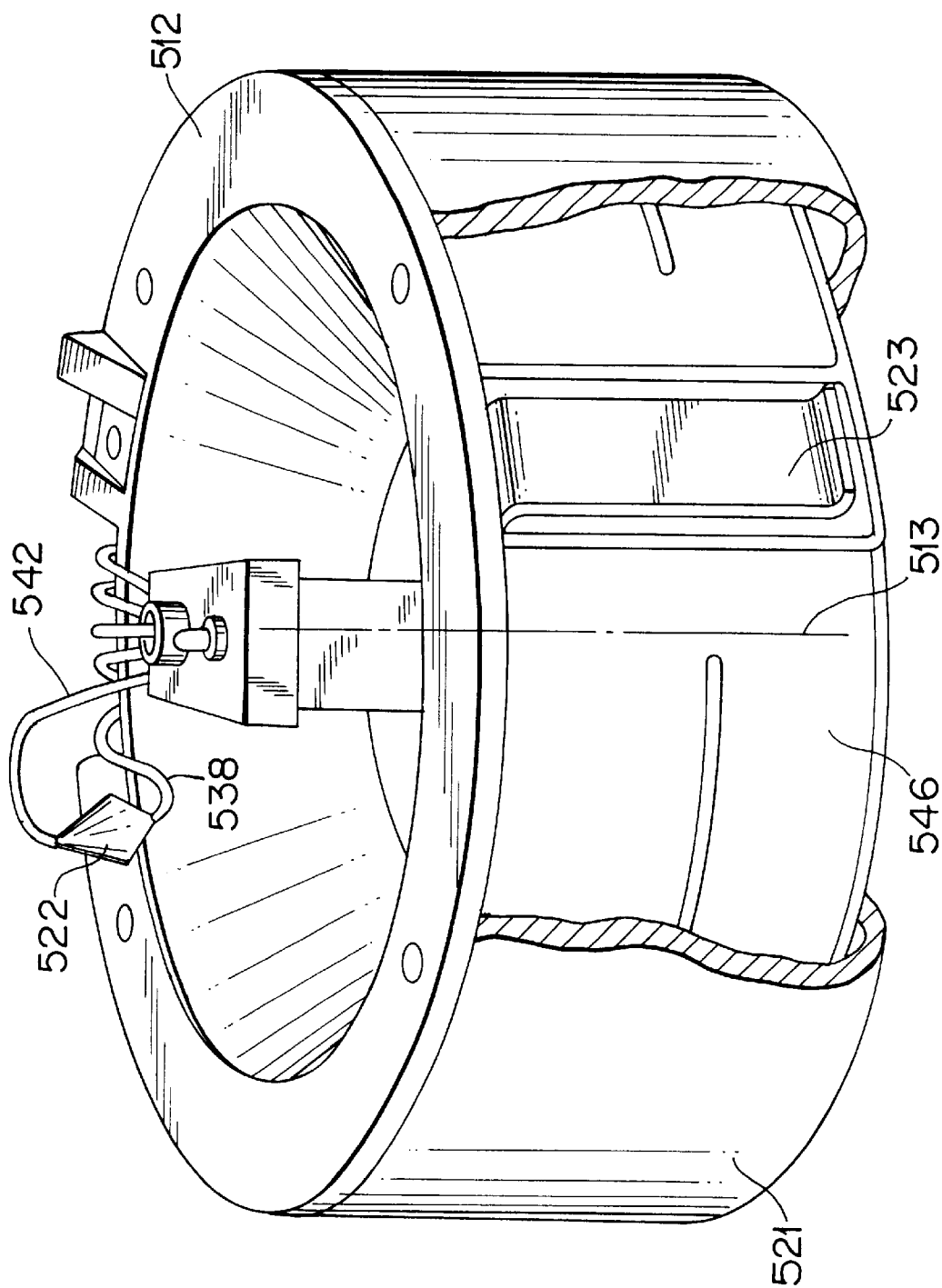
FIG. 10 is a perspective view of an alternate embodiment of a centrifuge apparatus of the invention.

FIG. 10 illustrates another embodiment of the invention. In this embodiment a fluid chamber 522 is mounted on a centrifuge rotor 512. The rotor 512 includes an outer bowl 521 and a clip 523 for holding a separation chamber 546 formed in an elongated flexible tubular or belt shape from plastic material. The device depicted in FIG. 10 separates particles, in particular blood components, within the separation chamber 546 by generating centrifugal force. For further details concerning the configuration and operation of this device, refer to U.S. Pat. No. 5,362,291 to Williamson, Iv, U.S. Pat. No. 5,360,542 to Brown et al., and U.S. Pat. No. 5,078,671 to Dennehey et al., the disclosures of which are incorporated herein by reference.

The fluid chamber 522 is mounted or held on the centrifuge rotor 512 with an outlet 532 facing substantially toward an axis of rotation 513 of the centrifuge rotor 512. Inflow tubing 542 supplies liquid and particles to the fluid chamber 522 after the particles undergo an initial separation within a portion of the separation chamber 546. In a similar fashion, outflow tubing 538 conveys substances from the fluid chamber 522 to another portion of the separation chamber 546.

In using the embodiment shown in FIG. 10, particles carried by a liquid are separated in the separation chamber 546 according to density and size differences of the particles. After being initially separated, the liquid and particles, for example plasma carrying platelets and white blood cells, flow into the fluid chamber 522. Within fluid chamber 522, a saturated fluidized particle bed forms to further separate particular particles from the flowing liquid.

Figure 11:
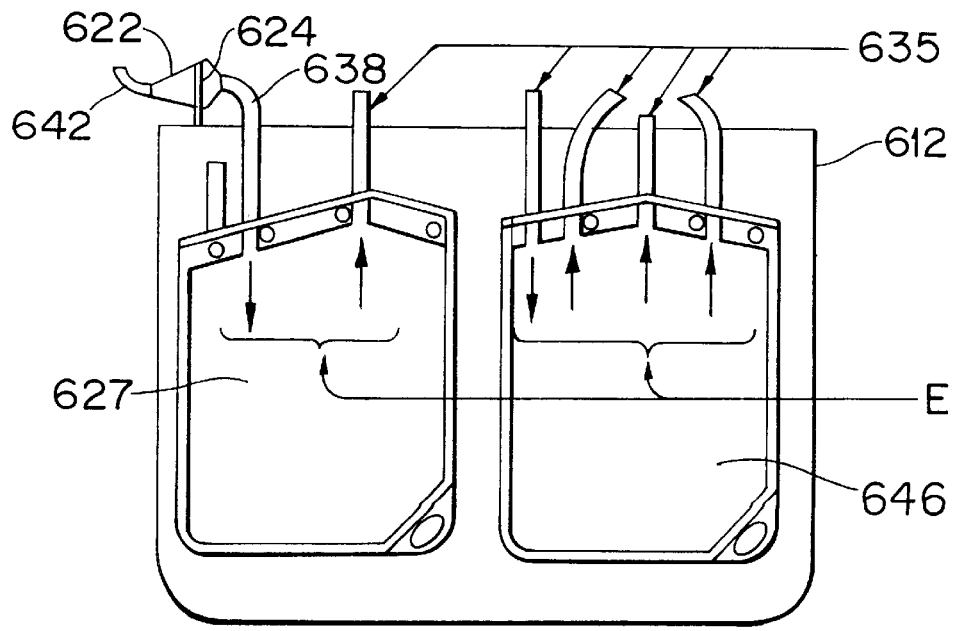
FIG. 11 is a cross-sectional schematic view of another embodiment of the centrifuge apparatus of the invention.
Figure 12:
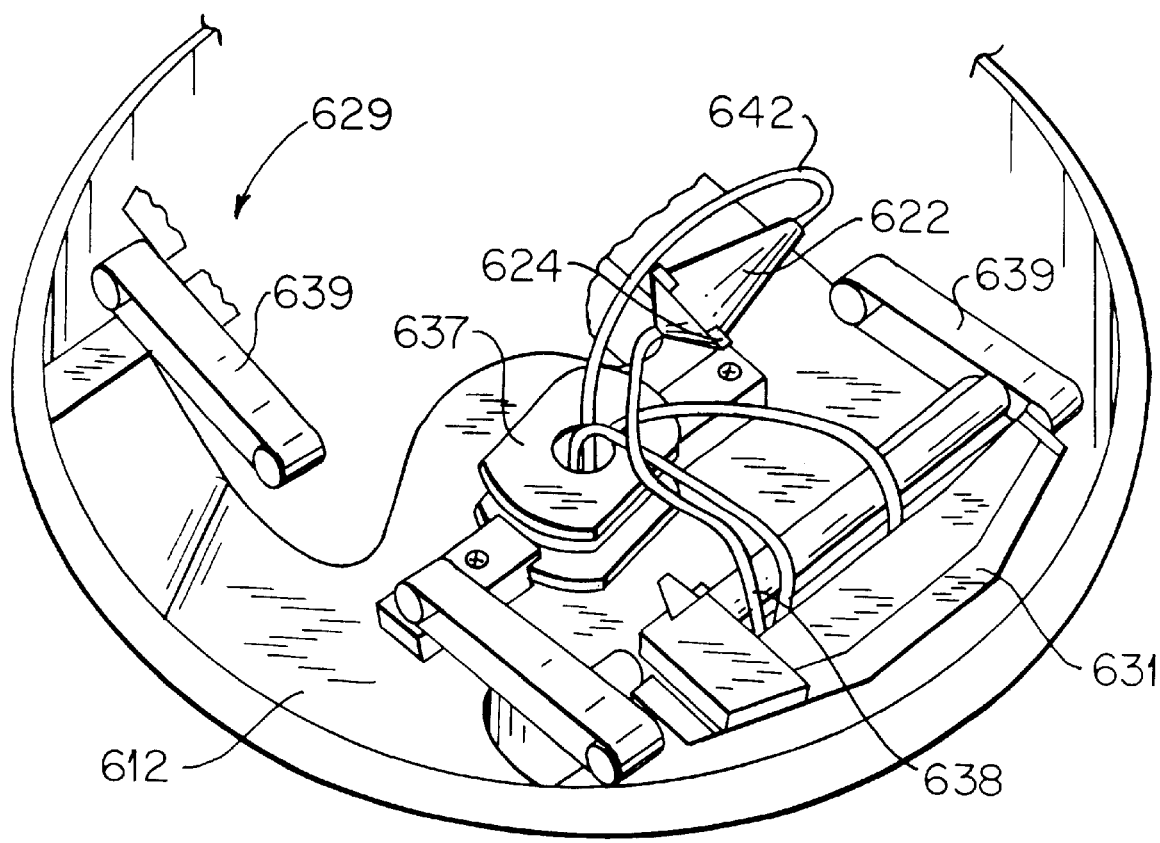
FIG. 12 is a partial perspective view of the centrifuge apparatus of FIG. 11.

Yet another embodiment of the invention is illustrated in FIGS. 11 and 12. This embodiment includes both a separation chamber 646 shaped as a container and a collection container 627. Holders 629, 631 hold separation chamber 646 and container 627, respectively, on a centrifuge rotor 612. Flow lines 635, 638 provide fluid flow to and from the separation chamber 646 and container 627 as indicated by the arrows labelled with the symbol "E" shown in FIG. 11. Further components include a restraining collar 637 and container holder clamp assemblies 639. Particles are separated according to density and size differences within the separation chamber 646 in response to centrifugal force. For further details of how this device is configured and operates, refer to Baxter Heathcare Corporation's CS-3000® Plus Blood Separator Operator's Manual (7-19-3-136), the disclosure of which is incorporated herein by reference.

As depicted in FIGS. 11 and 12, a holder 624 holds a fluid chamber 622 on the rotor 612. Inflow tubing 642 conveys liquid and particles initially separated in separation chamber 646 into the fluid chamber 622. In addition, an outflow tubing 638 fluidly couples the fluid chamber 622 to the collection container 627. With this configuration, a saturated fluidized particle bed may be formed in the fluid chamber 622, as explained with respect to the above embodiments, to filter particles.

FIG. 13 illustrates a further embodiment of the invention. This embodiment includes a separation chamber 746, preferably formed from rigid transparent plastic conduit, capable of being inserted into a centrifuge. An inlet 741 allows whole blood to flow into a first stage 743 of the separation chamber 746, so that red blood cells may be removed from a conduit 745, while platelet rich plasma flows through conduit 742. In addition, a conduit 747 and outlet 749 enable removal of platelet poor plasma and platelets, respectively, in a second stage 751. For further details regarding the structural configuration and operation of this embodiment, refer to the Brief Operating Instructions of the Fresenius MT AS 104 blood cell separator (4/6.90(OP)), the disclosure of which is incorporated herein by reference.

As shown in FIG. 13, a fluid chamber 722 may be coupled to the separation chamber 746. A saturated fluidized particle bed may be formed in the fluid chamber 722 to separate particles after initial particle separation in the separation chamber 746, in the manner described above.

In an alternate embodiment (not shown), the fluid chamber 722 may be coupled to outlet 749 of second stage 751. This alternate embodiment would allow for particles to be separated in a manner similar to the particle separation described for the embodiment shown in FIGS. 1–5.

FIG. 14 illustrates yet another embodiment of the invention. As shown, a separation chamber 846 and a first fluid chamber 822a are provided on a centrifuge rotor 812 in a manner similar to that of the embodiment of FIGS. 1–5. In addition, an outflow tubing 838 fluidly couples an outlet 832a of the fluid chamber 822a to an inlet 828b of an auxiliary fluid chamber 822b. Mounting brackets (holders) 824a, 824b maintain the fluid chamber and the auxiliary chamber 822a, 822b, respectively, at substantially the same radial distance from a rotation axis of the centrifuge rotor 812.

In using the embodiment shown in FIG. 14, centrifuge rotor 812 rotates to initially separate particles within separation chamber 846 according to density and/or sedimentation velocity. Liquid carries separated particles into the first fluid chamber 822a where particles further separate after formation of a saturated fluidized bed of particles or an elutriation field. Thereafter, the separated particles and liquid flow through tubing 838 into auxiliary fluid chamber 822b where particles are further separated by either a saturated fluidized bed of particles or an elutriation field. Thus, particles separate within chambers 822a, 822b by forming a saturated fluidized particle bed in one of the chambers 822a, 822b and an elutriation boundary in another of the chambers 822a, 822b, or, in the alternative, by forming either a saturated fluidized particle bed or an elutriation boundary in both of the chambers 822a, 822b.

Optionally the chambers 822a, 822b may have different dimensions, such as differing volumes, lengths or maximum diameters. For example, fluid chamber 822a may have a greater volume than that of auxiliary chamber 822b. These different dimensions allow for two different particle separations to take place within each of the chambers 822a, 822b.

The embodiment of FIG. 14 allows for multiple particle separations to take place simultaneously. Additionally, different types of particles may be harvested in one single procedure. Of course, one or more further fluid chambers may be added without departing from the scope of the invention. Furthermore, both of the chambers 822a and 822b may be cylindrical.

It will be apparent to those skilled in the art that various modifications and variations can be made to the structure and methodology of the present invention without departing from the scope or spirit of the invention.

The fluid chambers 122, 222, 322, 422, 1022, or 1022' depicted in the embodiments of FIGS. 6–9, 16 and 17, may be substituted for the fluid chambers 22, 522, 622, 722, 822*a* or 822*b*. Further, the invention can be modified by including supplemental fluid chambers or separation chambers. Although the invention has been described as having a separation chamber to initially separate particles from the liquid, the invention can be practiced without this initial separation taking place.

Although the controller 40 is described above as controlling rotor speed and flow rate, the controller 40 may also regulate other parameters. For example the controller may control the density or some other characteristic of the liquid used to carry particles into the fluid chamber.

In addition, while the invention is described herein in connection with blood component separation, the invention in its broadest sense is not so limited. The invention is applicable to other medical and non-medical uses.

The particles used to form the saturated fluidized bed in the chamber can differ from the particles within the fluid passing through the fluid chamber for filtration. Additionally, it is possible to initially form the saturated fluidized bed with an extremely high concentration of platelets having very few white blood cells.

Further, the fluid chamber of the invention may be used in a separation process involving elutriation or any other particle separation means without departing from the scope of the invention.

In view of the foregoing, it is intended that the present invention cover modifications and variations of this invention provided they come within the scope of the following claims and their equivalents.

What is claimed is:

1. An apparatus for filtering first particles from a liquid, the apparatus comprising:
    a motor;
    a centrifuge rotor coupled to the motor for rotation about an axis of rotation;
    a holder for holding a fluid chamber on the rotor with an outlet of the fluid chamber positioned closer to the axis of rotation than an inlet of the fluid chamber;
    means for supplying a liquid having at least first particles to the inlet of the fluid chamber; and
    means for maintaining a saturated fluidized bed of second particles within the fluid chamber when the holder holds the fluid chamber, the saturated fluidized bed of second particles filtering first particles from the liquid, the means for maintaining comprising:
        a controller for controlling at least one of the motor and the supplying means to maintain the saturated fluidized bed of second particles within the fluid chamber.

2. The apparatus of claim 1, wherein the means for supplying liquid having at least first particles to the inlet of the fluid chamber includes a pump for fluid connection to the fluid chamber, and wherein the controller regulates the pump.

3. The apparatus of claim 1, further comprising a passageway on the rotor for receiving a separation chamber capable of separating particles in response to centrifugal force.

4. The apparatus of claim 3, wherein the separation chamber includes a conduit and the passageway on the rotor receives the conduit.

5. The apparatus of claim 4, wherein the passageway includes a ridge positioned therein for contacting the conduit to form a dam in the conduit.

6. The apparatus of claim 3, wherein the passageway has a generally annular shape.

7. The apparatus of claim 3, wherein an upper portion of the passageway includes an opening to permit mounting of the separation chamber in the passageway.

8. The apparatus of claim 1, further comprising a second holder on the rotor for receiving a separation container.

9. The apparatus of claim 1, wherein the controller increases a supply of liquid having at least first particles to the fluid chamber by sequentially decreasing a rotational speed of the rotor, and then increasing both rotational speed of the centrifuge rotor and a flow of liquid having at least first particles provided by the supplying means.

10. The apparatus of claim 1, further comprising an auxiliary fluid chamber holder for holding an auxiliary fluid chamber on the rotor with an outlet of the auxiliary fluid chamber positioned closer to the axis of rotation than an inlet of the auxiliary fluid chamber.

11. An apparatus for separating particles from a liquid, the apparatus comprising:
    a motor;
    a centrifuge rotor coupled to the motor for rotation about an axis of rotation;
    a holder for holding a fluid chamber on the rotor with an outlet of the fluid chamber positioned closer to the axis of rotation than an inlet of the fluid chamber; and
    an elongated, generally annular passageway on the rotor for receiving a separation conduit capable of separating particles in response to centrifugal force, the separation conduit being flow connected to the fluid chamber.

12. The apparatus of claim 11, further comprising a separation conduit mounted within the passageway and a fluid chamber mounted within the holder.

13. The apparatus of claim 11, wherein an upper portion of the passageway includes an opening to permit mounting of the separation conduit in the passageway.

14. The apparatus for separating particles from a liquid, the apparatus comprising:
    a motor;
    a centrifuge rotor coupled to the motor for rotation about an axis of rotation;
    a holder for holding a fluid chamber on the rotor with an outlet of the fluid chamber positioned closer to the axis of rotation than an inlet of the fluid chamber; and
    a passageway on the rotor for receiving a separation conduit capable of separating particles in response to centrifugal force, the separation conduit being flow connected to the fluid chamber, and the passageway including a ridge positioned therein for contacting the separation conduit to form a dam in the separation conduit.

15. An apparatus for separating portions of a substance, the apparatus comprising:
    a centrifuge rotor for generating a centrifugal field;
    a fluid chamber connected to the rotor, the fluid chamber having an inlet and outlet;
    means for supplying a substance to the chamber, the substance including at least particles;
    means for establishing a saturated fluidized bed of the particles within the fluid chamber;
    means for supplying a substance to be filtered to the fluid chamber; and means for maintaining the saturated fluidized bed of particles in the chamber so that at least a first portion of the substance to be filtered is retained in the fluid chamber while at least a second portion of the substance to be filtered passes through the fluid chamber.

16. The apparatus of claim 15, further comprising means in fluid communication with the fluid chamber for separating particles from liquid.

17. The apparatus of claim 16, wherein the separating means includes a separation conduit on the rotor.

18. The apparatus of claim 16, wherein the separating means includes a separation container on the rotor.

19. The apparatus of claim 16, further comprising a passageway on the rotor, the separating means being mounted in the passageway.

20. The apparatus of claim 19, wherein the passageway includes a ridge positioned therein for contacting the separation means to form a dam in the separation means.

21. The apparatus of claim 19, wherein the passageway has a generally annular shape.

22. The apparatus of claim 19, wherein an upper portion of the passageway includes an opening to permit mounting of the separation means in the passageway.

23. The apparatus of claim 15, wherein the rotor is rotatable about an axis of rotation and wherein the apparatus further comprises a holder on the rotor, the fluid chamber being mounted in the holder so that the outlet of the fluid chamber is positioned closer to the axis of rotation than the inlet of the fluid chamber.

24. An apparatus for separating particles from a liquid, the apparatus comprising:

a motor;

a centrifuge rotor coupled to the motor for rotation about an axis of rotation;

a holder for holding a fluid chamber on the rotor with an outlet of the fluid chamber positioned closer to the axis of rotation than an inlet of the fluid chamber; and a generally annular shaped passageway on the rotor for receiving a separation conduit capable of separating particles in response to centrifugal force, the separation conduit being flow connected to the fluid chamber, and the holder being positioned closer than the passageway to the axis of rotation.

* * * * *